(12) United States Patent
Campiani et al.

(10) Patent No.: US 6,391,870 B2
(45) Date of Patent: May 21, 2002

(54) PYRROLO [2,1-B][1,3]BENZOTHIAZEPINES WITH ATYPICAL ANTIPSYCHOTIC ACTIVITY

(75) Inventors: Giuseppe Campiani, Chianciano Terme; Vito Nacci, Siena; Patrizia Minetti; Maria Assunta Di Cesare, both of Rome, all of (IT)

(73) Assignee: Sigma-Tau Industrie Farmaceutiche Riunite S.p.A., Rome (IT)

(*) Notice: Subject to any disclaimer, the term of this patent is extended or adjusted under 35 U.S.C. 154(b) by 0 days.

(21) Appl. No.: 09/769,740

(22) Filed: Jan. 26, 2001

Related U.S. Application Data

(63) Continuation of application No. PCT/IT99/00420, filed on Jul. 27, 1999.

(30) Foreign Application Priority Data

Jul. 28, 1998 (IT) .......................................... MI98A1748

(51) Int. Cl.[7] ........................ C07D 513/00; A61K 31/38
(52) U.S. Cl. .................................. 514/211.12; 540/551
(58) Field of Search ...................... 514/211.12; 540/551

*Primary Examiner*—Bruck Kifle
(74) *Attorney, Agent, or Firm*—Nixon & Vanderhye

(57) ABSTRACT

Polycondensated heterocycles with a pyrrole[2,1-b][1,3] benzothiazepine structure of the following formula (I)

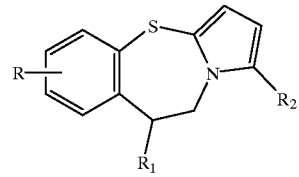

(I)

where the groups are defined as in the description are disclosed. As compared to known antipsychotic agents, these compounds present substantial activity associated with a simultaneous reduction in unwanted extrapyramidal symptoms. These compounds can be formulated in pharmaceutical compositions for the treatment of psychoses such as, for example, schizophrenia.

19 Claims, No Drawings

PYRROLO [2,1-B][1,3]BENZOTHIAZEPINES WITH ATYPICAL ANTIPSYCHOTIC ACTIVITY

This application is a continuation of PCT/IT99/00420, filed Jul. 27, 1999.

The present invention relates to the field of antipsychotic drugs, in particular to polycondensated heterocycles with a pyrrolo[2,1-b][1,3]benzothiazepine structure.

STATE OF THE ART

The intervention of dopamine and dopaminergic neurons in the pathology of a variety of psychiatric and neurological disorders has been amply documented (Caine, D. B., Therapeutics and Neurology; Blackwell Scientific Publications, Oxford 1980, p. 281). In addition, it is also known that drugs which are active on dopamine receptors may play an important role in the therapy of such disorders; there is therefore considerable interest in the effects of dopamine agonist and antagonist compounds on dopaminergic receptors, particularly with a view to their therapeutic implications.

Chlorpromazine and aloperidol have long been the treatment of choice for acute and chronic schizophrenia. It has been postulated that these drugs relieve the positive symptoms of the disease by blocking dopaminergic transmission in certain areas of the brain. Chlorpromazine and aloperidol are defined as "typical neuroleptic agents": their action is characterised by remission of the symptoms of schizophrenia, accompanied, however, by unwanted extrapyramidal collateral symptoms (motor disorders, catalepsy, hyperprolactinaemia, etc.). The elimination of these adverse effects therefore constitutes an important objective in the development of new neuroleptic therapies.

Clinical trials have demonstrated that not only dopamine antagonists but also $5-HT_2$ antagonist compounds are capable of improving the symptoms of schizophrenia, in particular, it has been observed that the co-administration of $5-HT_2$ antagonists and "typical" antipsychotic agents reduces the incidence of extapyramridal symptoms as compared to treatment with neuroleptic agents alone (Psychopharmacol., 99, 1989, S18–S27; Niemegeers et al. in $5-HT_2$ Receptor Antagonists in Schizophrenia, Racagni Ed., Elsevier Publishers, 1991, Vol. 1, pp. 535–537).

Further developments in this sense have led to the generation of drugs with a mixed antagonist component, i.e. which are active on different receptors.

Clozapine (8-chloro-11-(4-methyl-1-piperazinyl)-5H-dibenzo[b,e][1,4]diazepine) is an antipsychotic agent capable of simultaneously antagonising dopamine on D2 receptors and serotonin on $5-HT_2$ receptors. This new action profile, called "atypical", allows schizophrenia to be treated with a lower incidence of extrapyramidal symptoms (J. Med. Chem., 39, 1996, pp. 1172–1188).

Unfortunately, the occurrence of cases of agranulocytosis has limited the therapeutic use of this drug (Lancet. 1975, 2, 657).

Octoclothepin (8-chloro-10-(4-methylpiperazino)-10,11-dihydrodibenzo[b,f]thiepin) is a compound partly endowed with "atypical" activity. Its pharmacological activity has been studied in relation to the optical isomers of this compound (J. Med. Chem., 1991, 34, 2023–2030): a slightly greater effect on schizophrenia by the (S) form is unfortunately associated with a greater incidence of extrapyramidal effects, so that its use has been withdrawn from clinical trials. The (R) isomer presents a more "atypical" profile, with fewer side effects, but also an inferior general potency.

Moreover, the two isomers prove to be endowed with the same activity as $5-HT_2$ and $D_1$ antagonists.

In view of the studies cited above, the need for antipsychotic agents with substantial therapeutic activity and without side effects remains unsatisfied. In particular, the search continues for antipsychotic agents which present greater neuroleptic activity and a lower incidence of extapyramidal effects.

It has now surprisingly been found that polycondensated heterocycles with a pyrrolo[2,1-b][1,3]benzothiazepine are endowed with an interesting pharmacological profile as antipsychotic activity.

ABSTRACT OF THE INVENTION

The present invention describes polycondensated heterocycles with a pyrrolo[2,1-b][1,3]benzothiazepine structure. As compared to known antipsychotic agents, the compounds according to the invention present substantial activity associated with a simultaneous reduction in unwanted extrapyramidal symptoms. The compounds object of the invention described herein can be formulated in pharmaceutical compositions for the treatment of psychoses such as, for example, schizophrenia.

Accordingly, it is an object of the present invention polycondensated heterocycles with a pyrrolo[2,1-b][1,3]benzothiazepine structure as disclosed in the formula (I) below.

Another object of the present invention is a process for the preparation of said compounds.

Still another object of the present invention is the use of said compounds as medicaments, in particular as antipsychotic agents, for the treatment of psychosis, such as schizophrenia, paranoid states, manic-depressive states, affective disorders, social withdrawal, personality regression, or hallucinations.

In its industrial aspects, the present invention provides pharmaceutical compositions comprising at least a compound of the invention.

DETAILED DESCRIPTION OF THE INVENTION

The invention described herein relates to new derivatives with a neuroleptic action, corresponding to the following structural formula (I):

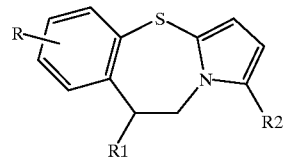

where:
R=H, Cl, Br, F, I, $C_1$–$C_4$ alkoxy, $C_1$–$C_4$ alkylthio, $C_1$–$C_4$ alkyl, $C_5$–$C_6$ cycloalkyl;
$R_1$=dialkylamine, 4-alkyl-1-piperazinyl, 4-hydroxyalkyl-1-piperazinyl, 1-imidazolyl, 4-alkyl-1-piperidinyl
$R_2$=hydrogen, $C_1$–$C_4$ alkoxy, $C_1$–$C_4$ alkylthio;
and the pharmaceutically acceptable salts thereof.

The formula (I) derivatives possess a chiral carbon atom in position 9 on the benzothiazepine ring. The invention described herein comprises both the formula (I) derivative in racemic form and the single (R) and (S) isomers, separately.

In formula (I), R preferably represents bromine, chlorine, fluorine or hydrogen, more preferably chlorine or fluorine;

$R_1$ preferably a 4-methylpiperazinyl group; and $R_2$ preferably hydrogen.

Preferred derivatives according to the invention are the products:

(±)-9-(4-methylpiperazin-1-yl)-9,10-dihydropyrrolo[2,1-b][1,3]benzothiazepine, hereinafter referred to as (±)-3a;

(±)-7-chloro-9-(4-methylpiperazin-1-yl)-9,10-dihydropyrrolo[2,1-b][1,3]benzothiazepine, hereinafter referred to as (±)-3b (ST1455);

(+)-7-chloro-9-(4-methylpiperazin-1-yl)-9,10-dihydropyrrolo[2,1-b][1,3]benzothiazepine, particularly preferred, hereinafter referred to as (+)-3b (ST1460)

(±)-7-fluoro-9-(4-methylpiperazin-1-yl)-9,10-dihydropyrrolo[2,1-b][1,3]benzothiazepine, hereinafter referred to as (3c) (ST1456);

(±)-7-fluoro-9-(4-ethylpiperazin-1-yl)-9,10-dihydropyrrolo[2,1-b][1,3]benzothiazepine (4c) (ST1457);

(±)-7-fluoro-9-[4-(2'-hyroxyethylpiperazin-1-yl]-9,10-dihydropyrrolo[2,1b][1,3]benzothiazepine (5c) (ST1458);

The invention described herein also relates to new, effective methods of synthesis to obtain the new pyrrolo[2,1-b][1,3]benzothiazepine structures. One of the problems encountered was that of realising a cyclisation method that made it possible to obtain the particular formula (I) tricyclic system with high yields.

The various synthesis methods described herein include a cyclisation reaction of a derivative comprising a phenyl group and a pyrrole group, where the cyclisation leads to the formation of a [1,3] thiazepine ring. The result of said cyclisation reaction is preferably a pyrrolobenzothiazepinone, which can be transformed into a formula (I) derivative by substituting the keto group on the thiazepine ring with a group selected from the definitions given above for the radical $R_1$.

A process for the synthesis of formula (I) products is illustrated in Scheme 1A in its essential steps, and in Scheme 1B in detail.

Scheme 1A

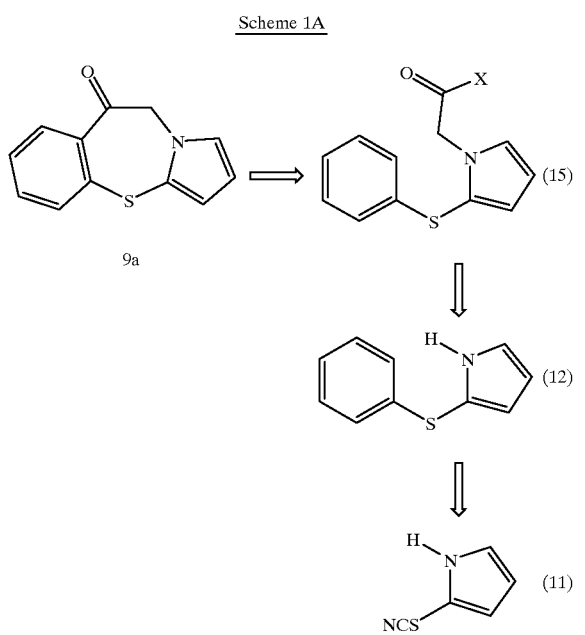

Scheme 1B

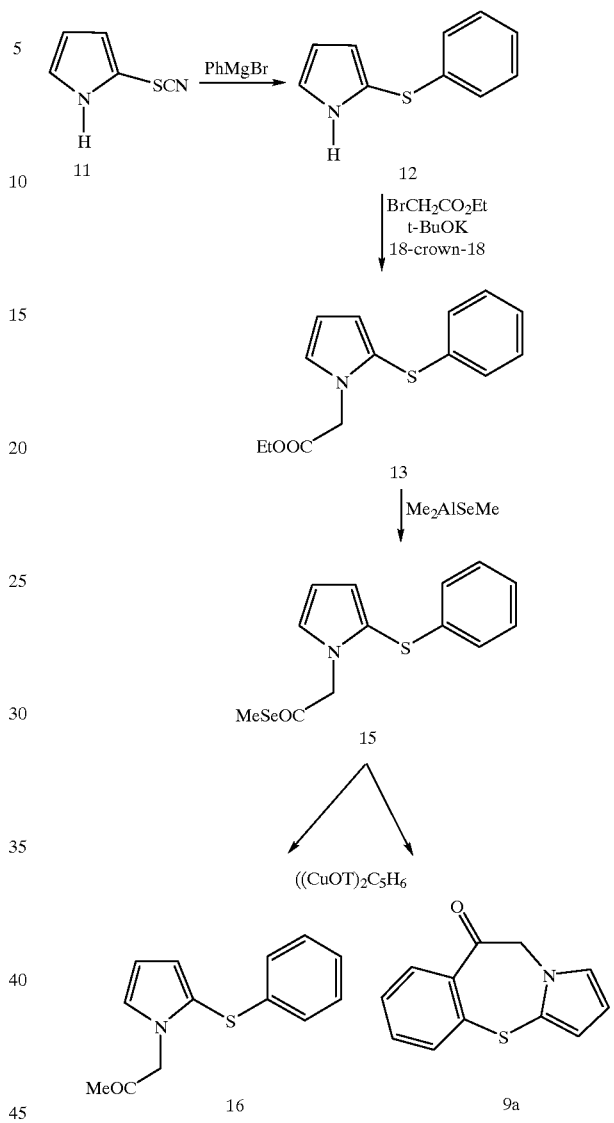

With reference to Scheme 1B, the process involves the reaction of 2-thiocyanate-pyrrole (11) with phenyl magnesium bromide to form thioether (12). Thioether (12), subjected to esterification and transacylation reactions, gives rise to the derivative methylselenolate (15) comprising a phenyl group and a pyrrole group. Derivative (15) is then subjected to a cyclisation reaction, with formation of product (9a) (pyrrolobenzothiazepinone). The cyclisation reaction is conducted in the presence of a crystalline complex of triflate copper (I) and benzene.

Lastly, product (9a) is transformed into a formula (I) derivative by means of subsequent modifications of the keto group on the thiazepine ring to obtain derivatives with $R_1$ as described above.

One preferred process for the synthesis of formula (I) products is illustrated in Scheme 2A in its essential steps and in Schemes 2B in detail.

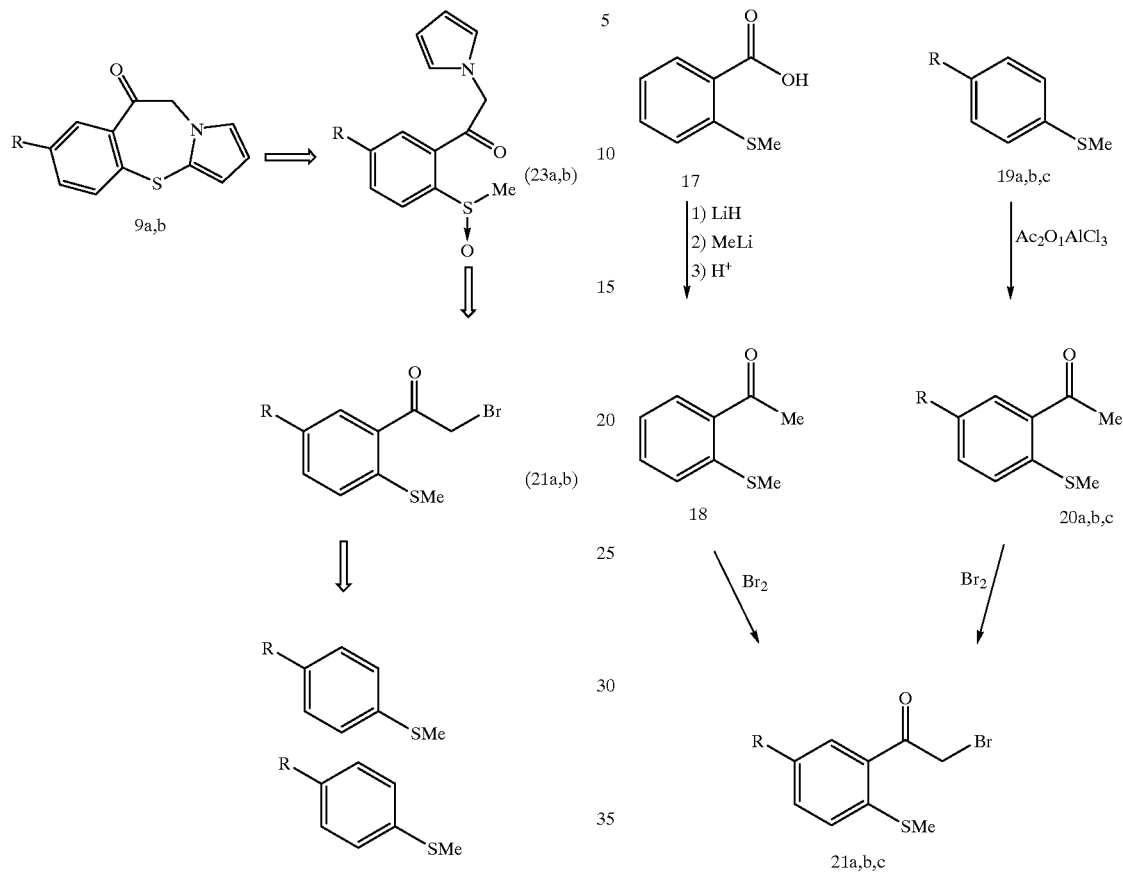
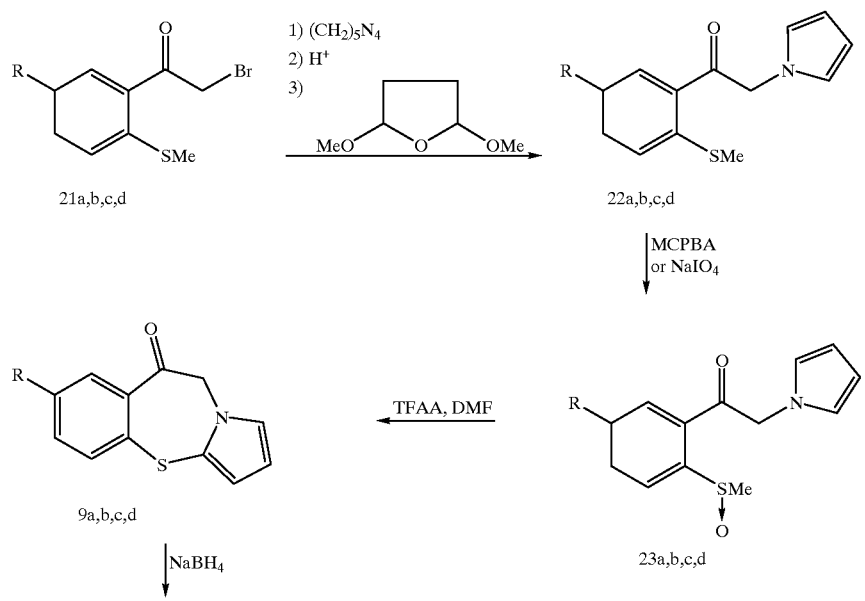

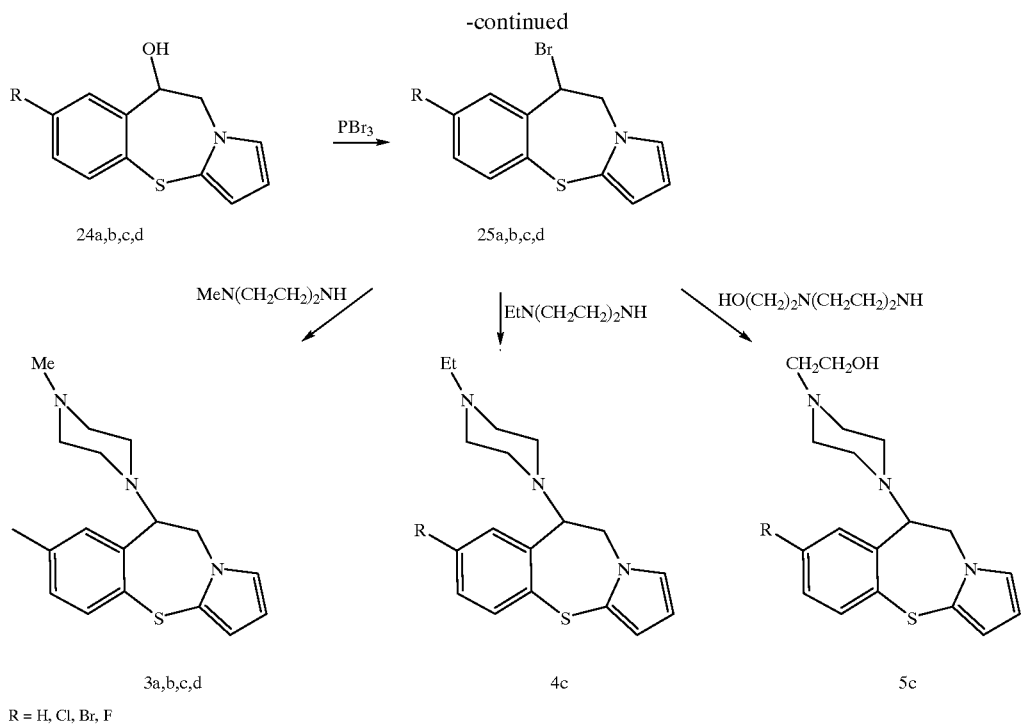

3a,b,c,d     4c     5c

R = H, Cl, Br, F

With reference to Schemes 2B/1 and 2B/2, the process involves the formation of the intermediate product (21a,b,c, SCHEME 2B/1; bromophenylethanone; 21a: R=H; 21b: R=Cl; 21c=F). As far as the intermediate compound 21d is concerned, the synthetic path is outlined in the Scheme C below.

The intermediate product (21a,b,c,d) is transformed into the corresponding sulphoxide (23a,b,c,d). The latter, when subjected to a cyclisation reaction, leads to the formation of the product (9a,b,c,d) (pyrrolobenzothiapinone). The cyclisation reaction is conducted in the presence of trifluoracetic anhydride and dimethylformamide.

This second synthesis method is preferred in that the cyclisation reaction and consequent formation of the thiazepine ring occur with distinctly greater yields.

Products (9a), (9b), (9c) and (9d), obtained with the different synthesis methods described above are then transformed into a formula (I) derivative by substituting the keto group with a group selected from the definitions given above for the radical $R_1$.

SCHEME C

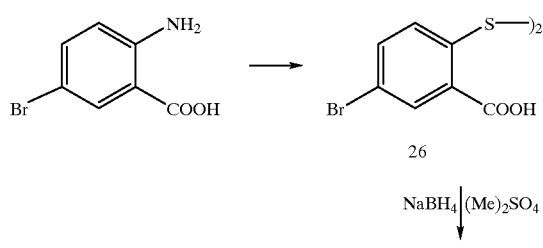

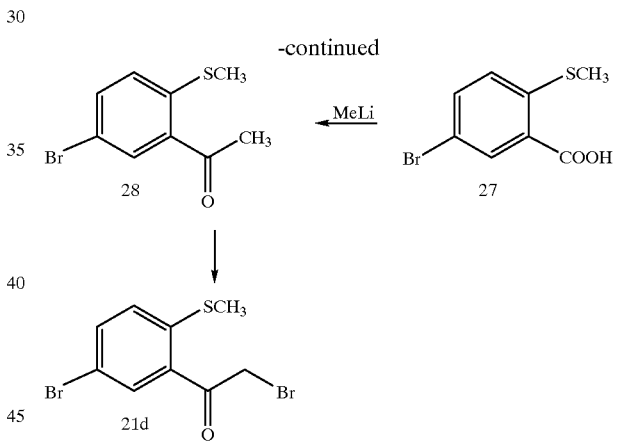

It is then always possible to resolve the racemic products, however they are obtained, into the two active isomers by means of fractionated crystallisation of the diastereoisomeric salts obtained by salification with an optically active acid, such as tartaric acid, dibenzoyltartaric acid, camphoric acid, or camphor-sulphonic acid.

A detailed description of the above-mentioned synthesis methods is presented in the experimental part.

A further subject of the invention described herein consists in pharmaceutical compositions comprising formula (I) derivatives in combination with pharmacologically acceptable excipients and vehicles and optionally with additional active ingredients which are useful in the treatment of psychoses.

Examples of such optional active ingredients are the phenothiazines (e.g. chlorpromazine), the thiaxanthenes (e.g. chlorprothixene, titothixene), the butyrophenones (e.g. aloperidol), the dihydroindolones (e.g. molindone), the dibenzoxazepines (e.g. loxapine), the Rauwolfia alkaloids, etc.

Formula (I) compounds can be formulated in solid, liquid or semisolid pharmaceutical forms. Examples of liquid formulations are injectable solutions or solutions for oral use, syrups, elixirs, suspensions and emulsions. Examples of solid forms are tablets, capsules, microcapsules, powders and granulates.

Formula (I) compounds are endowed with a pronounced neuroleptic and antipsychotic activity. This enables them to be used in the prevention and treatment of psychoses such as schizophrenia, paranoid states, manic-depressive states, affective disorders, social withdrawal, personality regression, hallucinations, appetite disorders (anorexia) and related disorders. Additional indications may be analgesia/anaesthesia, neuroleptic anaesthesia, anxiety manifestations in the elderly, and extrapyramidal disturbances. The invention described herein therefore includes the use of formula (I) products in the preparation of medicinal products which are useful for the prevention and treatment of said disorders.

Some of the formula (I) products have an interesting $D_3:D_1$ ratio, indicating them useful in the treatment of the negative symptoms of schizophrenia involving the emotional and cognitive spheres such as, for instance, dementia.

As documented in the experimental part, the "atypicity" of the neuroleptic action of formula (I) derivatives makes it possible to treat the above-mentioned pathologies effectively, at the same time reducing to a minimum the extrapyramidal side effects normally associated with the classic antipsychotic agents. The substantial receptor activity that characterises these compounds also makes it possible to considerably reduce the dose necessary to achieve a therapeutic response, thus reducing toxicity and accumulation phenomena. The reduction of the daily dose is an aspect of particular interest in the treatment of chronic diseases such as schizophrenia, which require prolonged eposure to the drug.

Formula (I) compounds can be administered over a dosage range generally varying from 0.02 to 200 mg/kg, depending upon the severity of the disease to be treated and its acute or chronic component. Doses outside the range indicated are, however, possible in particular conditions, under the supervision of a doctor.

The invention is now illustrated by means of the following examples.

Experimental Part
1. Chemistry
1.1 Synthetic Approaches

The synthesis of the new pyrrolo[2,1-b][1,3] benzothiazepine structure was accomplished by adopting the two retrosynthetic approaches described in Schemes 1A and 2A. The synthesis is based on a cyclisation method to obtain the pyrrolobenzothiazepinone intermediate products 9a,b. Scheme 1A gives our retrosynthetic analysis of compound 9a. When pyrrolo was treated with copper thiocyanate in methanol, thyocyanation occurred in a few minutes, obtaining 2-thiocyanopyrrolo 11 with good yields. The Grignard reaction with phenylmagnesium bromide (12), followed by alkylation with ethyl bromoacetate, produced ester 13 with a high overall yield.

Ester 13 may serve as a starting product in carrying out the cyclisation to 9a, on the basis of an acylation reaction promoted by copper(I). In fact, dimethyl aluminium methylselenolate was used to obtain selenoester 15. Like the thioesters, this selenoester could be used in the carbon-carbon bond formation reaction. Consequently, by exposure of 15 to the highly reactive crystalline complex of triflate copper(I) and benzene [(CuOTf)$_2$PhH], the tricylic compound 9a was obtained together with ketone 16 and other unidentified reaction products.

Another synthesis method, shown in Scheme 2A, was based on a thionium ion intermediate. This made it possible to prepare the key tricyclic intermediates 9a,b,c,d in conditions of Pummerer rearrangement, starting from sulphoxides, which in turn were prepared from 1-[2-(methylthio)phenyl]ethanones. As shown in Scheme 2B/1, the key intermediate products 21a,b,c were prepared by bromination of the corresponding phenylethanones 18 and 20, which in turn were prepared, respectively, by reaction of methyllithium and the lithium salt of 2-(methylthio)benzoic acid 17, or from (methylthio)benzene, 1-chloro- or 1-fluoro-4-(methylthio)benzene 19a,b,c, with a Friedels-Crafts reaction with acetic anhydride. Subsequently (SCHEME 2B/2), the bromophenylethanones 21a,b,c,d were transformed into the pyrrole derivatives 22a,b,c,d. Oxidation, for example with sodium periodate or 3-chloroperbenzoic acid (MCPBA) (23a,b,c,d), followed by exposure of these sulphoxides to trifluoracetic anhydride produced the ketones 9a,b,c,d with a yield of 40%. The mechanism proposed for the cyclisation stage is given in Scheme 2B/3.

Scheme 2B/3

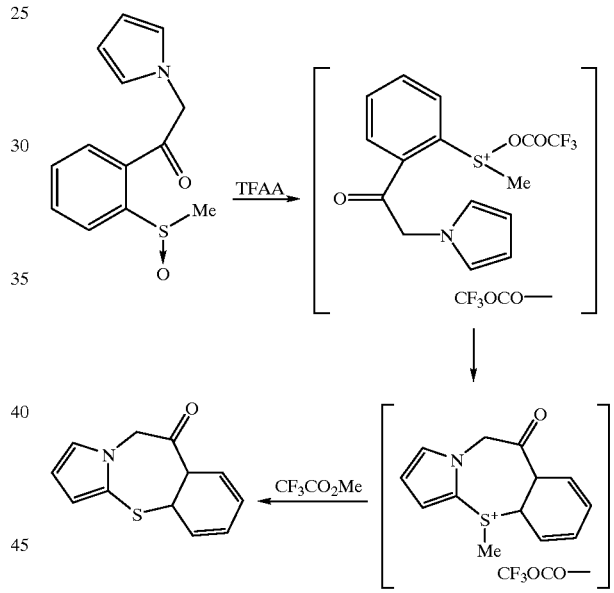

(1)

The "interrupted" Pummerer rearrangement started with activation of the oxygen of the sulphoxide followed by attachment of the pyrrole ring to the sulphur which shifted the trifluoroacetate ion. The sulphonium salt then underwent the shift of the methyl group, generating the new heterocyclic system and methyltrifluoroacetate. Starting from the ketones 9a,b,c,d (Fig. 2B/2), the piperazine ring was introduced according to a standard method. Reduction of ketones 9a,b,c,d then yielded the alcohols (±)-24a,b,c,d which were transformed into the corresponding derivatives (±)-25a,b,c,d by means of PBr$_3$. By treating (±)-25a,b,c,d with N-methylpiperazine, the end product (±)-3a,b,c,d was obtained. The thiazepine (±)-3a,b was resolved into the enantiomorphs (+)-3b and (−)-3b by means of HPLC, using a Chiralpak AD amylose column, or equivalent means.

1.2 Materials and Methods

The melting points were determined using an Electrothermal 8103 device and were not corrected. The IR spectra were recorded with Perkin-Elmer 398 and FT 1600 spectrophotometers. The $^1$H-NMR spectra were recorded with a Bruker 200 MHz spectrometer and a Varian 500 MHz spectrometer with TMS as internal standard; the chemical shift values (δ) are given in ppm and the coupling constants (J) in Hertz. All reactions were carried out in an argon atmosphere. Progress of the reactions was monitored by TLC on silica gel plates (Riedel-de-Haen, Art. 37341). Merck silica gel (Kieselgel 60) was used for the chromatography columns (70–230 mesh) and for the flash chromatography columns (230–400 mesh). Exacts were dried on $MgSO_4$ and the solvents removed at reduced pressure. The HPLC separation was carried out using a Chiralpak AD Amylose column (097-702-40808) (length×diameter=250 mm×10 mm). The elemental analyses were carried out on a Perkin-Elmer 240C elemental analyzer, and the results are within 0.4% of the theoretical value, unless otherwise specified. The yields refer to purified, non-optimised products.

1.3 Preparation of the Compounds

2-(phenylthio)pyrrole (12)

To a solution of phenyl magnesium bromide (prepared from bromobenzene (0.75 ml) and magnesium chips (0.19 g, 7.8 mmol) in anhydrous THF (20 ml), cooled to 0° C., was slowly added a solution of 2-thiocyanopyrrole 11 (0.5 g, 4.0 mmol) in anhydrous THF (20 ml). After stirring at 0° C. for 30 min, the mixture was poured into crushed ice and extracted with ethyl acetate. The organic phase was washed with 20% $NH_4Cl$, anhydrified and evaporated. The residue was purified by chromatography (35% hexane in chloroform) to give 0.6 g (93% yield) of 12 as colourless prisms: melting point 86–87° C. (hexane); IR ($CHCl_3$) 3420 cm$^{-1}$; $^1$H NMR ($CDCl_3$) δ8.20 (br s, 1H), 7.25–6.85 (m, 5H), 6.92 (m, 1H), 6.55 (m, 1H), 6.31 (m, 1H). Anal. ($C_9H_9NS$): C, H, N.

Ethyl ester of 2-(phenylthio)pyrrole-1-acetic acid (13)

To a mixture of 18-Crown-6 (20 mg, 0.074 mmol) and potassium terbutoxide (0.166 mg, 1.48 mmol) in anhydrous THF (5 ml) was added a solution of 12 (0.2 g, 1.14 mmol) in anhydrous THF (5 ml) under nitrogen. After 2 hours at ambient temperature, a solution of ethyl bromoacetate (0.254 ml, 2.28 mmol) in anhydrous THY (1 ml) was added dropwise. After stirring for 30 min at ambient temperature and the addition of 5 ml of water, the solvent was removed at reduced pressure and the residue extracted with EtOAc. The organic layers were washed with a saturated solution of NaCl, anhydrfied and evaporated. The residue was chromatographed (30% hexane in chloroform) to give 0.28 g (96% yield) of 13 as colourless prisms: melting point 101–102° C. (cyclohexane); IR ($CHCl_3$) 1760 cm$^{-1}$; $^1$H NMR ($CDCl_3$) δ7.25–6.90 (m, 5H); 6.61 (m, 1H), 6.31 (m, 1H), 4.68 (s, 2H), 4.05 (q, 2H, J=7.0 Hz), 1.14 (t, 3H, J=7.1 Hz). Anal. ($C_{14}H_{15}NO_2S$): C, H, N.

Methyl ester of 2-(phenylthio)pyrrole-1-selenoacetic acid (15)

A solution of dimethylaluminium methylselenolate (2.2 mmol) (prepared by heating a solution of trimethylaluminium in toluene with selenium in powder form for 2 hours at reflux temperature under argon) in anhydrous toluene (1.1 ml) was added dropwise to a solution of 13 (0.57 g, 2.2 mmol) in anhydrous dichloromethane (5 ml) cooled to 0° C., under nitrogen. The mixture was agitated at 0° C. for 45 min, heated to ambient temperature and stirred for another 45 min. Water (2 ml) was added and the mixture was extracted with EtOAc. The organic layers were washed with a saturated NaCl solution, anhydrified and evaporated. The crude product was purified by distillation (85° C./0.1 mm Hg) to give 0.6 g (97% yield) of 15 as a colourless oil: IR (t.q.) 1720 cm$^{-1}$; $^1$H NMR ($CDCl_3$) δ7.24–6.95 (m, 6H); 6.69 (m, 1H), 6.37 (m, 1H), 4.69 (s, 2H), 2.11 (s, 3H) m/z 311 (40, M$^+$), 188, 155, 109, 91 (100). Anal. ($C_{13}H_{13}SeNOS$): C, H, N.

1-[2-(methylthio)phenyl]ethanone (18)

To a suspension of lithium hydride (0.57 g, 6.7 mmol) in anhydrous 1,2-dimethoxyethane (5 ml), stirred vigorously, was added dropwise a solution of acid 17 (1.0 g, 5.9 mmol) in anhydrous 1,2-dimethoxyethane. The suspension was refluxed for 2,5 hours, cooled to −10° C. and added with methyl-lithium (4.2 ml, 6.7 mmol, 1,6 M) in the space of 30 min. The reaction mixture was stirred for 2 hours at ambient temperature. HCl 1N was added to the mixture, which was extracted with ethyl ether. The organic layers were washed with a saturated NaCl solution, anhydrified and concentrated. Chromatography of the crude product (5% benzene in dichloromethane) gave 0.78 g (79% yield) of 18 as colourless prisms, the spectroscopic data for which were identical to those reported in the literature.

1-[5-chloro-2-(methylthio)phenyl]ethanone (20b)

A mixture of 19b (1.0 g, 6.3 mmol), anhydrous aluminium chloride (1.88 g, 13.5 mmol) and carbon sulphide (20 ml) was heated to reflux under argon and acetic anhydride (0.46 ml, 6.3 mmol) was added dropwise. After reflux for 4 h, the solution was poured onto crushed ice arid 20 ml of HCl 6N were added. The mixture was extracted with EtOAc and the organic layers were washed with a saturated NaCl solution, anhydrified and concentrated. The oily residue was chromatographed (30% hexane in chloroform) to give 0.5 g (40% yield) of 20b as a waxy solid: IR (t.q.) 1670 cm$^{-1}$; $^1$H NMR ($CDCl_3$) δ7.83 (d, 1H, J=2.1 Hz); 7.44 (dd, 1H), 7.29 (d, 1H, J=8.1 Hz), 2.63 (s, 3H), 2.41 (s, 3H). Anal. ($C_9H_9ClOS$): C, H.

2-Bromo-1-[2-(methylthio)phenyl]ethanone (21a)

The title compound was obtained starting from 18 and following the procedure as described below to obtain 21c. 21a was obtained as colorless prism (69% yield):mp 81–82° C.(hexanes); IR (nujol) 1690 cm$^{-1}$, $^1$H NMR ($CDCl_3$) δ8.00–7.80 (m,2H), 7.35 (m,2H), 5.53 (s,2H), 2.27 (s,3H) Anal. ($C_9H_9BrOS$)C,H.

2-Bromo-1-[5-cloro-2(methylthio)phenyl]ethanone (21b)

The title compound was obtained starting from 20b and following the procedure as described below to obtain 21c. 21b was obtained as colorless prism (62% yield); mp 97–98° C.(hexanes); IR ($CHCl_3$) 1685 cm$^{-1}$; $^1$H NMR ($CDCCl_3$) δ7.98–7.73(m,3H), 5.57(s,2H), 2.31(s,3H). Anal.($C_9H_8BrClOS$) C,H.

1-[2-(methylthio)phenyl]-2-pyrrol-1-yl)ethanone (22a)

To a solution of 21a (2.1 g, 8.6 mmol) in 20 ml of anhydrous DMF, was added hexamethylene tetramine in portions. The solid formed was filtered, washed with chloroform and dried.

The hexamethylenetetrammonium salt thus obtained was added to a concentrated HCl solution (3 ml) in 8 ml of ethanol.

The mixture was stirred for 96 hours in the dark at ambient temperature. The white solid ($NH_4Cl$) was filtered and the solution vacuum-concentrated.

The residue was crystallised by ethanol, and 2-amino-1-[2-(methyl-thio)phenyl]ethanone hydrochloride was obtained with a yield of 78%; $^1$H NMR (DMSO-$d_6$) δ8.43 (br s, 2H); 8.11–7.31 (m, 5H), 4.59 (d, 2H, J=3.2 Hz), 2.46 (s, 3H). Anal. ($C_9H_{12}ClNOS$): C, H, N.

The 2-amino-1-[2-(methylthio)phenyl]ethanone hydrochloride was dissolved in an aqueous solution of sodium acetate, glacial acetic acid and 2.5 dimethoxy tetrahydrofuran. After stirring for 15 min at 100° C., the mixture was cooled and extracted with ethyl acetate. The organic layer was washed with $NaHCO_3$, dried and evaporated. The crude product was chromatographed ($CHCl_3$) to give 22a with a yield of 50%: melting point 113–114° C. (hexane); IR (nujol) 1690 $cm^{-1}$; $^1$H NMR ($CDCl_3$) δ7.74–7.23 (m, 4H), 6.66 (m, 2H), 6.21 (m, 2H), 5.25 (d, 2H, J=3.4 Hz), 2.44 (s, 3H). Anal. ($C_{13}H_{13}NOS$): C, H, N.

1-[5-chloro-2-(methylthio)phenyl]-2-pyrrol-1-yl) ethanone (22b)

Staring from 21b (5.58 g, 20.0 mmol), 2-amino-1-[5-chloro-2-(methyl-thio)phenyl]ethanone hydrochloride was obtained using the procedure described in the previous example: yield 75%; $^1$H NMR (DMSO-$d_6$) δ8.41 (br s, 2H); 8.10–7.28 (m, 3H), 4.48 (d, 2H, J=3.2 Hz), 2.42 (s, 3H). Anal. ($C_9H_{11}Cl_2NOS$): C, H, N.

Starting from 2-amino-1-[5-chloro-2-(methylthio)phenyl] ethanone hydro-chloride, the titre compound was obtained as colourless prisms using the procedure described to obtain 22a; 51% yield; melting point 124–125° C. (hexane); IR (nujol) 1720 $cm^{-1}$; $^1$H NMR ($CDCl_3$) δ7.62 (d, 1H, J=2.3 Hz); 7.45 (dd, 1H, J=8.2, 2.3 Hz), 7.29 (d, 1H, J=8.2 Hz), 6.65 (m, 2H), 6.22 (m, 2H), 5.21 (s, 2H), 2.43 (s, 3H); $^{13}$C NMR ($CDCl_3$) δ194.2, 140.6, 134.5, 132.4, 130.1, 128.9, 127.7, 121.8, 109.2, 56.6, 16.6. Anal. ($C_{13}H_{12}ClNOS$): C, H, N.

1-[2-(methylsulphinyl)phenyl]-2-pyrrol-1-yl) ethanone (23a)

To a suspension of sodium periodate (0.55 g, 2.6 mmol) in methanol (7 ml) and water (1.4 ml) was added a solution of 22a (0.6 g, 2.6 mmol) in methanol (2 ml). After stirring for 24 hours at ambient temperature the sodium iodate was removed by filtration and the filtrate was evaporated. The residue was chromatographed (5% EtOAc in dichloromethane) to give 0.59 g of 23a (92% yield) as colourless prisms: melting point 174–175° C. (ethanol); IR (nujol) 1710, 1090 $cm^{-1}$; $^1$H NMR ($CDCl_3$) δ8.42–7.64 (m, 4H), 6.66 (m, 2H), 6.27 (m, 2H), 5.44 (0.5 ABq, 1H, J=18.0 Hz), 5.27 (0.5 ABq, 1H, J=18.0 Hz), 2.80 (s, 3H). Anal. ($C_{13}H_{13}NO2S$); C, H, N.

1-[5-chloro-2-(methylsulphinyl)phenyl]-2-pyrrol-1-yl)ethanone (23b)

The titre compound was prepared starting from 22b (1.1 g, 4.45 mmol) using the procedure described above for 23a: colourless prisms (89% yield): melting point 218–219° C. (ethanol); IR (nujol) 1710, 1080 $cm^{-1}$; $^1$H NMR ($CDCl_3$) δ8.37 (d, 1H, J=8.0 Hz); 7.85 (m, 2H), 6.66 (m, 2H), 6.28 (m, 2H), 5.40 (0.5 Abq, 1H, J=17.7 Hz), 5.25 (0.5 ABq, 1H, J=17.8 Hz), 2.79 (s, 3H); $^{13}$C NMR ($CDCl_3$) δ193.4, 149.6, 136.9, 134.7, 132.5, 128.8, 127.0, 121.8, 109.8, 55.7, 44.3. Anal. ($C_{13}H_{12}ClNO_2S$): C, H, N.

9,10-dihydropyrrolo[2,1-b][1,3]benzothiazepin-9-one (9a)

Method A: to a highly reactive solution of the crystalline complex of triflate copper(I) and benzene (0.81 g, 1.6 mmol) in anhydrous benzene (20 ml), cooled to 0° C., was added a solution of selenoester 15 (0.5 g. 1,6 mmol) in anhydrous benzene (11 ml) and the mixture was left to stir at ambient temperature for 16 hours. Ethyl ether (10 ml) was added, the organic phase was washed with ammonia 6N, anhydrified and concentrated. The crude product was chromatographed (5% hexane in dichloromethane) to give 51 mg of 9a (12% yield) as colourless prisms. Ketone 16 (55% yield) was also recovered as a dense oil. Compound 9a: melting point 94–95° C. (hexane); IR ($CDCl_3$) 1690 $cm^{-1}$; $^1$H NMR ($CDCl_3$) δ8.14–7.30 (m, 4H); 6.88 (m, 1H), 6.42 (m, 1H), 6.12 (m, 1H), 5.15 (s, 2H); $^{13}$C NMR ($CDCl_3$) δ190.9, 136.1, 133.3, 132.3, 130.8, 127.6, 123.9, 120.2, 114.4, 109.2, 57.6. MS m/z 265 (10, M$^+$), 215 (100), 187, 154,115, 97. Anal. ($C_{12}H_9NOS$): C, H, N.

Compound 16: IR (t.q.) 1670 $cm^{-1}$; $^1$H NMR ($CDCl_3$) δ7.22–6.81 (m, 6H); 6.70 (m, 1H), 6.42 (m, 1H), 4.61 (s, 2H), 2.20 (s, 3H). MS m/z 231 (100, M$^+$). Anal. ($C_{13}H_{13}NOS$): C, H, N.

Method B: trifluoroacetic anhydride (1.0 ml, 7.4 mmol) was added dropwise to just distilled N,N-dimethylformamide (8 ml) cooled to 0° C. After stirring for 20 min at 0° C., a solution of 23a (1.0 g, 4.0 mmol) was added in just distilled N,N-dimethylformamide (24 ml) and after 15 min at 0° C. and 1 hour at ambient temperature, the pH of the dark red solution was brought to 7 with NaOH 1N and the mixture was stirred for another 30 min. Extraction with dichloromethane, anhydrification of the exacts and evaporation of the solvent gave an oily residue which was chromatographed (30% hexane in chloroform). Compound 9a was obtained with a 45% yield.

7-chloro-9,10-dihydropyrrolo[2,1-b][1,3] benzothiazepin-9-one (9b)

The titre compound was obtained with a yield of 42%, as colourless prisms, starting from 23b and adopting the procedure as described for 9a (Method B): melting point 106–107° C. (hexane); IR ($CDCl_3$) 1690 $cm^{-1}$; $^1$H NMR ($CDCl_3$) δ8.14 (d, 1H, J=2.2 Hz); 7.49 (d, 1H, J=8.1 Hz), 7.38 (dd, 1H, J=8.0, 2.3 Hz), 6.88 (m, 1H), 6.43 (m, 1H), 6.12 (m, 1H), 5.14 (s, 2H); $^{13}$C NMR ($CDCl_3$) δ189.7, 138.3, 133.3, 137.3, 134.1, 133.1, 132.2, 131.9, 124.1, 119.5, 114.7, 109.5, 57.3. MS m/z 250 (20, M$^+$), 249 (100), 221, 216, 188, 158, 110. Anal. ($C_{12}H_8ClNOS$): C, H, N.

(±)-9,10-dihydro-9-hydroxypyrrolo[2,1-b][1,3] benzothiazepine (24a)

To a solution of 9a (61 mg, 0.23 mol) in anhydrous methane (1 ml), cooled to 0° C. and under nitrogen, were added aliquots of sodium borohydride (80 mg, 0.23 mmol). After stirring for 1 hour at 0° C., the reaction was stopped with water (1 ml) and the mixture extracted with EtOAc. The organic layers were washed with brine, anhydrified and concentrated. The residue was chromatographed (15% EtOAc in dichloromethane) to give 24a (64 mg, 92% yield) as colourless prisms: melting point 101–102° C. (ethanol); IR (nujol) 3300 $cm^{-1}$; $^1$H NMR ($CDCl_3$) δ7.47–7.12 (m, 4H), 6.86 (m, 1H), 6.33 (m, 1H), 6.02 (m, 1H), 5.08 (m, 1H), 4.89 (dd, 1H, J=13.9, 1.7 Hz), 4.28 (dd, 1H, J=13.9, 6.0 Hz), 2.05 (d, 1H, J=9.6 Hz). Anal. ($C_{12}H_{11}NOS$): C, H, N.

(±)-7-chloro-9,10-dihydro-9-hydoxypyrrolo[2,1-b] [1,3]benzothiazepine (24b)

The titre compound was obtained starting from 9b (112 mg, 0.45 mmol) using the procedure described above: 88% yield; melting point 118–119° C. (ethanol); IR (CHCl$_3$) 3300 cm$^{-1}$; $^1$H NMR (CDCl$_3$) δ7.48 (d, 1H, J=2.1 Hz); 7.32 (d, 1H, J=8.0 Hz), 7.15 (dd, 1H, J=8.1, 2.1 Hz), 6.88 (m, 1H), 6.34 (m, 1H), 6.11 (m, 1H), 5.02 (m, 1H), 4.85 (dd, 1H, J=13.9, 1.9 Hz), 4.29 (dd, 1H, J=13.9, 6.6 Hz), 2.10 (dd, 1H, J=9.6 Hz). Anal. (C$_{12}$H$_{10}$ClNOS): C, H, N.

(±)-9-bromo-9,10-dihydropyrrolo[2,1-b][1,3]benzothiazepine (25a)

To a solution of 24a (0.26 g, 1.0 mmol) in anhydrous ethyl ether (4 ml) was added dropwise a solution of PBr3 (0.13 g, 0.5 mmol) in anhydrous ethyl ether (1 ml) and the reaction mixture was kept at reflux temperature for 2 hours under nitrogen. Anhydrous ethanol was added (0.2 ml) and the resulting solution was heated to reflux temperature for another hour. Five ml of an aqueous solution of 5% Na$_2$CO$_3$ were then added, the organic phase was separated, anhydrified and evaporated. The crude product was chromatographed (hexane and chloroform 1:1) to give 25a (0.2 g, 64% yield) as colourless prisms: melting point 115–116° C. (cyclohexane); $^1$H NMR (CDCl$_3$) δ7.46–7.09 (m, 4H); 6.93 (m, 1H), 6.39 (m, 1H), 6.12 (m, 1H), 5.75 (dd, 1H, J=6.9, 2.6 Hz), 5.07 (dd, 1H, J=14.7, 2.6 Hz), 4.61 (dd, 1H, J=14.7, 6.9 Hz). Anal. (C$_{12}$H$_{10}$BrNOS): C, H, N.

(±)-9-bromo-7-chloro-9,10-dihydropyrrolo[2,1-b][1,3]benzothiazepine (25b)

The titre compound was obtained starting from 24b (0.31 g, 1.6 mmol) using the procedure described above: 51% yield; melting point 106–107° C. (cyclohexane); $^1$H NMR (CDCl$_3$) δ7.45 (d, 1H, J=2.1 Hz); 7.27 (d, 1H, J=8.6 Hz), 7.11 (dd, 1H, J=8.6, 2.1 Hz), 6.92 (m, 1H), 6.39 (m, 1H), 6.12 (m, 1H), 5.63 (dd, 1H, J=7.0, 2.3 Hz), 5.06 (dd, 1H, J=14.4, 2.3 Hz), 4.61 (dd, 1H, J=14.0, 7.0 Hz). $^{13}$C NMR (CDCl$_3$) δ139.9, 134.1, 133.2, 131.7, 131.5, 128.9, 125.6, 119.6, 114.6, 108.1, 51.2, 51.0. Anal. (C$_{12}$H$_9$BrClNOS): C, H, N.

EXAMPLE 1

(±)-9-(4-methylpiperazin-1-yl)-9,10-dihydropyrrolo[2,1-b][1,3]benzo-thiazepine (3a)

A mixture of 25a (0.65 g, 2.0 mmol) and N-methylpiperazine (1.1 ml, 10.0 mmol) was heated to 130° C. for 2 hours under argon, cooled, poured onto crushed ice and extracted with ethyl ether. The organic extracts collected were washed with brine, anhydrified and concentrated. The residue was chromatographed (EtOAc) to give 0.45 g (75% yield) of 3a as colourless prisms: melting point 206–207° C. (hexane); $^1$H NMR (CDCl$_3$) δ7.49–7.09 (m, 4H); 6.87 (m, 1H), 6.29 (m, 1H), 4.68 (dd, 1H, J=14.4, 8.6 Hz), 4.51 (dd 1H, J=14.4, 3.7 Hz), 2.56–2.34 (m, 8H), 2.23 (s, 3H); $^{13}$C NMR (CDCl$_3$) δ138.1, 134.6, 132.9, 130.4, 127.3, 126.9, 123.9, 121.7, 113.3, 107.7, 66.1, 55.9, 48.8, 46.6. 46.1. MS m/z 299 (100, M$^+$), 219, 200, 167, 149, 113. Anal. (C$_{17}$H$_{21}$N$_3$S): C, H, N.

EXAMPLE 2

(±)-7-chloro-9-(4-methylpiperazin-1-yl)-9,10-dihydropyrrolo[2,1-b][1,3]benzothiazepine (3b) (ST1455)

The titre compound was obtained starting from 25b (0.3 g, 0.95 mmol) using the procedure described above. 3b was obtained as colourless prisms (68% yield): melting point 210–211° C. (hexane); $^1$H NMR (CDCl$_3$) δ7.51 (d, 1H, J=2.4 Hz); 7.30 (d, 1H, J=8.5 Hz), 7.06 (dd, 1H, J=8.5, 2.4 Hz), 6.86 (m, 1H), 6.29 (m, 1H), 6.05 (m, 1H), 4.71 (dd, 1H, J=14.0, 8.6 Hz), 4.45 (dd, 1H, J=14.0, 3.4 Hz), 3.95 (dd, 1H, J=8.6, 3.4 Hz), 2.65–2.25 (m, 8H), 1.42 (s, 3H); $^{13}$C NMR (CDCl$_3$) δ140.1, 133.2, 133.0, 132.4, 131.6, 127.3, 123.9, 121.1, 113.6, 107.9, 65.9, 55.8, 55.7, 47.7, 45.9, 44.9, 26.8. MS m/z 333 (10, M$^+$), 250, 233 (100), 201, 166, 139. Anal. (C$_{17}$H$_{20}$ClN$_3$S): C, H, N. The dihydrochloride salt (named hereinafter ST1468) was obtained by dissolving an analytical sample in HCl 1N in methanol. The solvent was evaporated and the residue recrystallised (methanol and ethyl ether 1:1). Anal. (C$_{17}$H$_{22}$Cl$_3$N$_3$S), C, H, N.

EXAMPLE 3

Semipreparatory Chiral Separation of (±)-3b

First of all, the hydrochloride salt of (±)-3b was purified on a short column filled with silica gel, using dichloromethane and methanol (9:1) as the eluent. The purified solvent was converted to the free base. Evaporation of the solvent gave an oily residue which was dissolved in isopropanol and the solution was diluted with hexane until the 95:5 ratio was obtained. For the separation of the enantiomers, a 10–15 mg/ml concentration of the racemic mixture was made. A mixture of hexane (plus 0.1% triethylamide) and isopropanol was used as the mobile phase.

A gradient-type mixer maintained the ratio between the solvents hexane and isopropanol at 95:5. Injection amounts were 100 μl per injection. The enantiomers were collected using a fraction collector. Only fractions with a signal above 10% (10 mV) of the total scale were collected. The amounts with signals below 10% were collected separately and used for a second purification. The purity of both enantiomers was determined by weighing the trace peaks separately.

(+)-3b: $^1$H NMR (500 Mhz, CDCl$_3$) δ7.52 (d, 1H, J=2.4 Hz); 7.32 (d, 1H, J=8.3 Hz), 7.09 (dd, 1H, J=2.4, 8.3 Hz), 6.88 (m, 1H), 6.30 (m, 1H), 6.07 (m, 1H), 4.71 (dd, 1H, J=8.8, 14.2 Hz), 4.50 (dd, 1H, J=3.9, 14.7 Hz), 3.97 (dd, 1H, J=3.4, 8.8 Hz), 2.55 (m, 4H), 2.40 (m, 4H), 2.27 (s, 3H); $^{13}$C NMR (500 MHz, CDCl$_3$) δ139.9, 133.0, 132.9, 132.3, 131.6, 127.3, 123.8, 121.0, 113.5, 107.9, 88.2, 65.8, 55.6, 48.6, 45.9, 45.8; purity (ee) 94.6%; [α]$_D$=+46.0° (c 0.48, MeOH). The respective dihydrochloride, obtained as in the case of compound (±)3b, was named ST1469.

(−)-3b: $^1$H NMR (500 Mhz, CDCl$_3$) δ7.53 (d, 1H, J=2.3 Hz); 7.32 (d, 1H, J=8.3 Hz), 7.09 (dd, 1H, J=6.8 Hz), 6.88 (m, 1H), 6.30 (m, 1H), 6.07 (m, 1H), 4.71 (dd, 1H, J=9.3, 14.5 Hz), 4.48 (dd, 1H, J=3.4, 14.2 Hz), 3.98 (dd, 1H, J=2.9, 8.8 Hz), 2.49 (m, 8H), 2.27 (s, 3H); $^{13}$C NMR (500 MHz, CDCl$_3$) δ140.0, 133.0, 132.9, 132.3, 131.6, 127.3, 123.8, 121.0, 113.5, 107.9, 88.2, 65.8, 55.6, 48.6, 45.9, 45.8; purity (ec) 98%; [α]$_D$=−47.9° (c 0.54, MeOH). The respective dihydrochloride, obtained as in the case of compound (±)3b, was named ST1470.

EXAMPLE 4

(±)-7-Fluoro-9-(4methylpiperazin-1-yl)-9,10-dihydropyrrolo[2,1b][1,3]benzothiazepine (3c) (ST1456)

The synthesis of the (3c) was been performed as described in Scheme 2B/1 and 2B/2 where c=F.

1-[5-Fluoro-2-(methylthio)phenyl]ethanone (20c)

A mixture of 4-fluorothioanisole (19c) (4 g, 28.13 mmol), anhydrous aluminium chloride (8.40 g, 63.02 mmol) and carbon disulphide (89 ml) was heated at reflux under argon atmosphere, and acetic arhydride (2.65 ml, 28.07 mmol) was added dropwise in 2 h. After refluxing for 24h, the solution was poured into crushed ice, water (62.48 ml) and concentrated hydrochloric acid (2.68 ml). The organic phase was separated and water extracted with dichloromethane (3×30 ml), the organic layers were washed with brine, dried and concentrated. The oily residue was chromatographed (50% petroleum ether 40–60° in dichloromethane) to afford 20c (2.98 g) as a colourless crystalline solid, mp 82.0–84.3° C. (58% yield). $^1$H NMR (CDCl$_3$) δ7.49–7.43 (dd, 1H, J=9.23, 2.44 Hz); 7.29–7.11 (m, 2H); 2.57 (s, 3H); 2.39 (s, 3H).

2-Bromo-1-[5-fluoro-2-(methylthio)phenyl]ethanone (21c)

To a stirring solution of 20c (2.07 g, 11.34 mmol), carbon tetrachloride (62 ml) and glacial acetic acid (2.07 ml) was added at room temperature a solution of bromine (μL 546.6, 10.66 mmol) in carbon tetrachloride (34 ml). The first drop was added and after 20 minutes the solution was added dropwise in 4 hours. After stirring for 16 hours the solvent was distilled and to the residue was added water and solid sodium bicarbonate (to pH 7), the organic phase was separated and water extracted with dichloromethane (3×30 ml), the organic layers were dried and evaporated. The crude product was chromatographed (70% petroleum ether 40–60° in dichloromethane) to give 1.90 g of 21c as a yellowish solid (64% yield). $^1$H NMR (CDCl$_3$) δ7.47–7.42 (dd, 1H, J=8.85, 2.84 Hz); 7.38–7.18(m, 2H); 4.42 (s, 2H); 2.43 (s, 3H).

1-[5-Fluoro-2-(methylthio)phenyl]-2-(pyrrol-1-yl) ethanone (22c)

To a stirring solution of hexamethylenetetramine (3.18 g, 22.70 mmol) in chloroform (29.6 ml) at room temperature was added dropwise in 5 minutes a solution of 21c (1.90 g, 7.20 mmol) in chloroform (16 ml). As soon as the solid formed the solution was rapidly filtered and the desired product was collected as a yellow amorphous solid that was washed with chloroform, dried and used for the following reaction; (99% yield).

A suspension of 1-[5-fluoro-2-(methylthio)phenyl] ethanon-2-hexaminium bromide (1.62 g, 4.02 mmol) in methanol (13.3 ml) was warmed to 0° C. and was added of concentrated hydrochloric acid (1.86 ml). The mixture was stirred for 96 hours in the dark at room temperature. The white solid (ammonium chloride) was removed by filtration and the obtained solution was evaporated. The residue was recrystallised from ethanol to give 2-amino-1-[5-fluoro-2-(methylthio)phenyl]ethanone hydrochloride as a yellow solid, that was used in the next step without further purification. (98% yield).

To a solution of 2-amino-1-[5-fluoro-2-(methylthio) phenyl]ethanone hydrochloride (4.54 g, 19.27 mmol) in water (29 ml), heated at 90° C., were added trihydrated sodium acetate (2.62 g, 19.27 mmol), glacial acetic acid (17 ml) and 2,5-dimethoxytetrahydrofuran (2.40 ml, 18.50 mmol). After 20 seconds at 90–100° C. the mixture was cooled and extracted with ethyl acetate. The organic layers were washed with a 20% solution of sodium bicarbonate and brine, dried and evaporated. The residue was chromatographed (50% petroleum ether 40–60° in dichloromethane) to afford 2.07 g of 22c as white crystals mp 133.2–134.0° C. (50% yield). $^1$H NMR (CDCl$_3$) δ7.39–7.15 (m, 34); 6.66–6.65 (m, 2H); 6.22–6.20 (m, 2H); 5.20 (s, 2H); 2.42 (s, 3H). MS m/z 252 (M$^+$+H), 234, 202 (100), 183, 169, 154, 141, 126, 109, 80.

1-[5-Fluoro-2-(methylsulfinyl)phenyl]-2-(pyrrol-1-yl)ethanone (23c)

To a stirred cooled solution of 1-[5-Fluoro-2-(methylthio) phenyl]-2-(pyrrol-1-yl)ethanone (22c) (1.76 g, 7.06 mmol) in dichloromethane (12 ml) was added dropwise in 30 minutes a solution of m-chloroperbenzoic acid (71.5% grade, 1.70 g, 7.06 mmol) in dichloromethane (10 ml). After stirring for 45 minutes at 0° C., the mixture was treated with a 5% solution of sodium carbonate in water (41 ml) and was stirred for 15 minutes at room temperature. The organic phase was separated and water was extracted with dichloromethane (3×10 ml). The organic layers were dried and evaporated, the residue was chromatographed (10% dichloromethane in ethyl acetate) to afford 1.02 g of 23c as white crystals that darkened rapidly (64% yield). $^1$H NMR (CDCl$_3$) δ8.42–8.35 (m, 1H); 7.61–7.51 (m, 2H); 6.68–6.62 (m, 2H); 6.26–6.24 (m, 2H); 5.41–5.17 (q, 2H, J=31.32, 17.87 Hz); 2.77 (s, 3H).

7-Fluoro-9,10-dihydropyrrolo[2,1-b][1,3] benzothiazepin-9-one (9c)

Trifluoroacetic anhydride (1.02 ml) was added dropwise under argon atmosphere to a freshly distilled N,N-dimethylformamide (8 ml) cooled to 0° C. After stirring for 20 minutes at 0° C. a solution of 23c (109 g, 4.12 mmol) in N,N-dimethylformamide (29 ml) was added. After 15 minutes at room temperature water (41 ml) was added to the dark yellow solution and pH was adjusted to 7 with sodium acetate, the mixture obtained was stirred at room temperature for 1 night. Extraction with dichloromethane, drying of the extracts, and evaporation of the solvent gave an oily residue which was chromatographed (30% petroleum ether 40–60° in dichloromethane). The compound 9c was crystallised from n-hexane as yellowish crystals mp 133.8–134.2° C. (20% yield). $^1$H NMR (CDCl$_3$) δ7.82–7.76 (m, 1H);7.55–7.49 (m, 1H); 7.18–7.09 (m, 1H); 6.88–6.87 (m, 1H); 6.42–6.40 (m, 1H); 6.12–6.09 (m, 1H); 5.14 (s, 2H). MS m/z 233 (100) (M$^+$), 205, 200, 172, 126.

(±)-7-Fluoro-9,10-dihydro-9-hydroxypyrrolo[2,1-b] [1,3]benzothiazepine (24c)

To a solution of 9c (0.037 g 0.16 mmol) in dry tetrahydrofuran (0.5 ml) and dry methanol (0.7 ml), cooled to 0° C. under argon atmosphere, was added in portions sodium borohydride (0.09 g, 0.16 mmol). After stirring for 1 hour at 0° C. the reaction was quenched with a saturated solution of ammonium chloride (1 ml), the solvent was removed and the mixture was extracted with ethyl acetate (3×2 ml). The organic layers were dried and evaporated, the crude product was chromatographed (30% petroleum ether 40–60° in dichloromethane) to give 24c 0.036 g (96% yield). 1H NMR (CDCl$_3$) δ7.40–7.33 (m, 1H); 7.24–7.18 (m, 1H); 6.93–6.84 (m, 2H); 6.33–6.31 (m, 1H); 6.11–6.08 (m, 1H); 5.12–5.04 (m, 1H); 4.91–4.83 (dd, 1H, J=14.22, 2.25 Hz); 4.34–4.24 (dd, 1H, J=14.02, 6.51 Hz); 2.09–2.04 (d, 1H, J=9.83 Hz).

(±)-9-Bromo-7-fluoro-9,10-dihydropyrrolo[2,1-b][1, 3]benzothiazepine (25c)

To a solution of 24c (0.17 g 0.71 mmol) in dry ethyl ether (3 ml) was added dropwise a solution of phosphorus tribromide (μL 33.5, 0.36 mmol) in dry ethyl ether (0.7 ml); the reaction mixture was refluxed for 2 hours under argon atmosphere. After cooling to room temperature dry ethanol (μL 143) was added and the resulting solution was heated at reflux for 1 hour. Then 4 ml of aqueous sodium carbonate was added; the organic phase was separated, dried and evaporated. The crude product was chromatographed (50% petroleum ether 40–60° in dichloromethane) to give 0.103 g of pure 25c (48% yield). $^1$H NMR (CDCl$_3$) δ7.35–7.16 (m, 2H); 6.92–6.82 (m, 2H); 6.39–6.37 (m, 1H); 6.13–6.09 (m, 1H); 5.69–5.64 (m, 1H); 5.10–5.01 (dd, 1H, J=14.57, 2.65 Hz); 4.70–4.59 (dd, 1H, J=14.88, 7.05 Hz).

EXAMPLE 5

(±)-7-Fluoro-9-(4methylpiperazin-1-yl)-9,10-dihydropyrrolo[2,1b][1,3]benzothiazepine(3c) ST1456

A mixture of 25c (0.05 g, 0.18 mmol) and N-methypiperazine (1 ml) was heated at 140° C. for 17 hours under argon atmosphere. The reaction mixture was then cooled, diluted with ethyl acetate (30 ml) and washed with brine. The organic layers were dried, evaporated and the oily residue was chromatographed (10% triethylamine in ethyl acetate) to afford 0.037 g of 3c as a colourless solid mp 213–214° C. (63% yield). 1H NMR (CDCl$_3$) δ7.37–7.26 (m, 2H); 6.85–6.76 (m, 2H); 6.29–6.27 (m, 1H); 6.06–6.03 (m, 1H); 4.78–4.67 (m, 1H); 4.49–4.40 (dd, 1H, J=14.19, 3.48 Hz); 3.99–3.93 (dd, 1H, J=8.97, 3.39 Hz); 2.64–2.37 (m, 8H); 2.25 (s, 3H). MS m/z 318 (100) (M$^+$+H), 277, 218, 185.

EXAMPLE 6

(±)-7-Fluoro-9-(4-ethylpiperazin-1-yl)-9,10-dihydropyrrolo[2,1-b][1,3]benzothiazepine(4c) ST1457

The desired product 4c was obtained starting from 25c (0.053 g, 0.178 mmol), using 4-ethylpiperazine (1 ml). The colourless liquid 4c was obtained with 73% yield. $^1$H NMR (CDCl$_3$) δ7.37–7.26 (m, 2H); 6.86–6.75 (m, 2H); 6.29–6.26 (m, 1H); 6.05–6.02 (m, 1H); 4.80–4.68 (m, 1H); 4.48–4.39 (dd, 1H, J=13.95, 3.78 Hz); 3.97–3.91 (dd, 1H, J=9.23, 3.65 Hz); 2.60–2.32 (m, 10H); 1.08–1.00 (t, 3H, J=7.33 Hz). MS m/z 332 (100) (M$^+$+H), 277, 218, 185, 115.

EXAMPLE 6

(±)-7-Fluoro-9-[4(2'-hydroxyethyl)piperazin-1-yl]-9,10-dihydropyrrolo[2,1b][1,3]benzothiazepine (5c) ST1458

A solution of 25c (0.065 g, 0.218 mmol) β-hydroxyethylpiperazine (μL 59, 0.218 mmol) and 2-buthanone (2 ml) was refluxed for 21 hours. The reaction mixture was then evaporated and to the residue was added water and was extracted with ethyl acetate, combined extracts were dried and evaporated. The crude product was chromatographed to give 5c as a colourless amorphous solid (69% yield). $^1$H NMR (CDCl$_3$) δ7.37–7.24 (m, 2H); 6.46–6.77 (m, 2H); 6.29–6.27 (m, 1H); 6.06–6.03 (m, 1H); 4.77–4.65 (m, 1H); 4.48–4.40 (dd, 1H, J=14.15, 3.46 Hz); 3.98–3.92 (dd, 1H, J=8.93, 3.50 Hz); 3.59–3.54 (t, 2H, J=5.37 Hz); 2.85 (bs, 1H); 2.57–2.47 (m, 10H). MS m/z 348 (100) (M$^+$+H), 288, 218, 185.

EXAMPLE 7

(±)-7-Bromo-9-(4-methylpiperazin-1-yl)-9,10-dihydropyrrolo[2,1-b][1,3]benzothiazepine (3d)

The synthesis of the (3d) was been performed as described in Scherme C and 2B/2 where d=Br.

Bis-(2-hydroxycarbonyl-4-bromo)phenyldisulphide (26)

To a cooled (0–5° C.) stirring solution of 2-amino-5-bromobenzoic acid (1 g, 4.63 mmol), sodium hydroxide (0.185 g, 4.63 mmol), water (7.71 ml) and sodium nitrite (0.32 g, 4.63 mmol) was slowly added a solution of concentrated hydrochloric acid (1.44 ml) in water (2.5 ml), the mixture was stirred at 0–5° C. for 1 h, than was neutralised with potassium carbonate and potassium acetate. The cold diazoniumn salt solution was run into a vigorously stirred solution of potassium ethyl xanthate (2.23 g, 13.89 mmol) and water (7.7 ml) previously heated at 75–80° C. and was maintaining this temperature during addition and for further 1 h. The reaction mixture was cooled to room temperature and stirred for 1 h. Than hydrogen peroxide (3.22 ml) was added and the solution was stirred for 1 night at room temperature. The mixture was filtered and the solution was acidified (on an ice bath) and filtered again. The product that was collected as a yellow amorphous solid was dissolved with aqueous sodium hydroxide and reprecipitated with hydrochloric acid to afford pure 26 (1.02 g) (95% yield). The compound was used in the next step without further purification.

1-[5-Bromo-(2-methylthio)phenyl]hydroxycarbonyl (27)

To a solution of (26) (1 g, 2.15 mmol) in 85% ethanol (17.2 ml) and sodium hydroxide, sodium borohydride (0.163 g) was added in portions. The resulting solution was stirred 30 minutes at room temperature and for additional 3 hours at reflux. Then ice was added and the mixture was stirred for 15 minutes at room temperature, a solution of sodium hydroxide (0.302 g, 7.55 mmol) in water (1.9 ml) and dimethyl sulphide (376 μL, 3.97 mmol) were added and the reaction mixture was stirred 2.5 hours at reflux. After cooling 1 drop of ammonium hydroxide 30% was added (to destroy the excess of sodium hydroxide), hydrochloric acid was added (pH 3). The solid obtained was collected by filtration. The crude product was chromatogaphed (4% formic acid, 20% ethyl acetate in toluene) to afford 1.017 g of 27 as a yellow solid (96% yield). $^1$H NMR (DMSO-d$_6$) δ7.95–7.94 (d, 1H, J=2.69 Hz); 7.72–7.66 (dd, 1H, J=8.80, 1.95 Hz); 7.29–7.25 (d, 1H, J=8.77 Hz); 2.37 (s, 3H).

1-[5-Bromo-(2-methylthio)phenyl]ethanone (28)

A stirred solution of (27) (0.1 g, 0.40 mmol) in dry tetrahydrofuran (3.03 ml) was cooled to 0° C. (ice bath) and treated with methyldithium (1.4 M solution in ether, 1.156 ml. 1.62 mmol). After 2 hours at 0° C. under stirring, trimethylchlorosilane (1.03 ml, 8.09 mmol) was rapidly added while stirring continued, the ice bath was removed and the reaction mixture was allowed to came to room temperature, then 1 N hydrochloric acid (3.05 ml) was added and the resulting two phase system was stirred at room temperature for 30 minutes. The organic phase was separated and water was extracted with ether (3×5 ml), the combined extracts were dried and evaporated. The crude product was chromatographed (30% petroleum ether 40–60° in dichloromethane) to afford 0.064 g of 28 as a yellowish solid mp 71.5–73.0° C. (64% yield). $^1$H NMR (CDCl$_3$) δ7.89–7.88 (d, 1H, J=1.91 Hz); 7.57–7.51 (dd, 1H, J=8.45, 2.48 Hz); 7.18–7.14 (d, 1H, J=8.48 Hz); 2.58 (s, 3H); 2.39 (s, 3H).

2-Bromo-1-[5-bromo-2-(methylthio)phenyl]ethanone (21d)

Starting from 28 (0.60 g, 2.43 mmol), the desired product 21d was obtained following the procedure described for 21c. The crude product was chromatographed (50% petroleum ether 40–60° in dichloromethane) to give the pure product 0.57 g. (72% yield). $^1$H NMR (CDCl$_3$) δ7.87–7.58 (d, 1H, J=1.60 Hz);7.48–7.42 (dd, 1H, J=8.05, 2.08); 7.12–7.16(d, 1H, J=8.06 Hz); 4.43 (s, 2H); 2.43 (s, 3H).

1-[5-Bromo-2-(methylthio)phenyl]-2-(pyrrol-1-yl) ethanone (22d)

The desired product 22d was obtained as white crystals, following the procedure described for 22c; mp 138.0–139.2° C. (32% yield). $^1$H NMR (CDCl$_3$) δ7.76–7.55 (d, 1H, J=1.92 Hz);7.60–754 (dd, 1H, J=8.43, 2.16 Hz);7.23–7.19 (d, 1H, J=8.82 Hz); 6.65–6.63 (m, 2H); 6.22–6.20 (m, 2H); 5.20 (s, 2H); 2.41 (s, 3H).

1-[5-Bromo-2-(methylsulfinyl)phenyl]-2-(pyrrol-1-yl)ethanone (23d)

Starting from 22d (0.27 g, 0.86 mmol), the desired product was obtained following the above-described procedure, as white crystals mp 138.0–139.2° C. (75% yield).$^1$H NMR (CDCl$_3$) δ8.30–8.25 (m, 1H); 8.0–7.96 (m, 2H); 6.64–6.62 (m, 2H); 6.27–6.25 (m, 2H); 5.43–5.18 (q, 2H, J=32.28, 17.92 Hz); 2.77 (s, 3H).

7-Bromo-9,10-dihydropyrrolo[2,1-b][1,3]benzothiazepin-9-one (9d)

The reaction to obtain 9d was carried out, accordingly the procedure described for 9c, using trifluoroacetic acid as solvent (0.63 ml) and adding solid 23d (0.20 g, 0.62 mmol) to the cold (0° C.) solution of trifluoroacetic acid and trifluoroacetic anhydride. The desired product 9d was obtained as yellowish crystals (64% yield). $^1$H NMR (CDCl$_3$) δ8.22–8.21 (d, 1H, J=1.99 Hz);7.56–7.51 (dd, 1H, J=8.28, 2.24 Hz); 7.42–7.38 (d, 1H, J=8.42 Hz); 6.87–6.86 (m, 1H); 6.43–6.41 (m, 1H); 6.12–6.09 (m, 1H); 5.13 (s, 2H). MS m/z 293 (100) (M$^+$), 265, 261, 232, 214, 186, 154, 115.

(±)-7-Bromo-9,10-dihydro-9-hydroxypyrrolo[2,1-b][1,3]benzothiazepine (24d)

Starting from 9d (0.12 g, 0.39 mmol), the desired product was obtained accordingly the procedure described for 24c (65% yield). $^1$H NMR (CDCl$_3$) δ7.63–7.62 (d, 1H, J=1.70 Hz); 7.32–7.21 (m, 2H); 6.88–6.87 (m, 2H); 6.34–6.32 (m, 1H); 6.12–6.09 (m, 1H); 5.02 (s, 1H); 4.90–4.82 (dd, 1H, J=13.86, 1.83 Hz); 4.36–4.25 (dd, 1H, J=14.18, 6.33 Hz); 1.99(s, 1H)

(±)-7,9-dibromo-9,10-dihydropyrrolo[2,1-b][1,3]benzothiazepine (25d)

Starting from 24d (0.07 g, 0.25 mmol) the title compound was obtained following the above-described procedure (36% yield). $^1$H NMR (CDCl$_3$) δ7.59 (m, 1H); 7.28–7.16 (m, 2H); 6.92–6.91 (m, 1H); 6.39–6.37 (m, 1H); 6.13–6.10 (m, 1H); 5.65–5.60 (dd, 1H, J=6.98, 2.57 Hz); 5.09–5.00 (dd, 1H, J=14.65, 2.35 Hz); 4.66–4.55 (dd, 1H, J=14.68, 7.03 Hz).

(±)-7-Bromo-9-(4-methylpiperazin-1-yl)-9,10-dihydropyrrolo[2,1-b][1,3]benzothiazepine (3d)

Starting from 25d (0.033 g, 0.092 mmol) the title compound was obtained following the procedure described for 3c (58% yield). $^1$H NMR (CDCl$_3$) δ7.64 (s, 1H); 7.35–7.21 (m, 2H); 6.86–6.84 (m, 1H); 6.29–6.26 (m, 1H); 6.06–6.02 (m, 1H); 4.73–4.61 (m, 1H); 4.49–4.40 (dd, 1H, J=14.30, 8.57 Hz); 3.98–3.92 (dd, 1H, J=8.64, 3.53 Hz); 2.57–2.37 (m, 11H).

2. Pharmacology
Experimental Procedures

In vitro Binding Assay
$D_1, D_2, D_3$ and 5-HT$_{2A}$ Affinity

Male CRL:CD(SD)BR-COBS rats (Charles River, Italy) were killed by decapitation (procedures involving animals and their care were conducted in conformity with the institutional guidelines that are in compliance with national (D.L. n. 116, G.U., suppl. 40, Feb. 18, 1992) and international laws and policies (EEC Council Directive 86/609, OJ L 358, 1, Dec. 12, 1987; Guide for the Care and Use of Laboratory Animals,U.S. National Research Council, 1996); their brains were rapidly dissected into the various areas (striatum for DA-$_1$ and DA-$_2$ receptors, olfactory tubercle for DA-$_3$ receptors and cortex for 5-HT$_{2A}$ receptors) and stored at −80° C. until the day of assay. Tissues were homogenised in about 50 volumes of Tris HCl, 50 mM, pH 7.4 (for DA-$_1$, DA-$_2$ and 5-HT$_{2A}$ receptors) or Hepes Na, 50 mM, pH 7.5 (for DA-$_3$ receptors), using an Ultra Turrax TP-1810 (2×20 sec.), and centrifuged at 50000 g for 10 min. The pellets were resuspended in fresh buffer, incubated at 37° C. for 10 min and centrifuged as before. The pellets were then washed once by resuspension in fresh buffer and centrifuged again. The pellets obtained were resuspended in the appropriate incubation buffer (Tris HCl, 50 mM, pH 7.1, containing 10 μM pargyline, 0.1% ascorbic acid, 120 mM NaCl, 5 mM KCl, 2 mM CaCl$_2$, 1 mM MgCl$_2$ for DA-$_1$ and DA-$_2$ receptors; Hepes Na, 50 mM, pH 7.5, containing 1 mM EDTA, 0.005% ascorbic acid, 0.1% albumin, 200 nM eliprodil for DA-$_3$ receptors) just before the binding assay.

[$^3$H]SCH 23390 (specific activity 70.3 Ci/mmol, NEN) binding to DA-$_1$ receptors was assayed in a final incubation volume of 0.5 ml, consisting of 0.25 ml of membrane suspension (2 mg tissue/sample), 0.25 ml of [$^3$H]ligand (0.4 nM) and 10 μl of displacing agent or solvent. Non-specific binding was obtained in the presence of 10 μM (−)-cis-flupentixol.

[$^3$H]Spiperone (specific activity 16.5 Ci/mmol, NEN) binding to DA-$_2$ receptors was assayed in a final incubation volume of 1 ml, consisting of 0.5 ml of membrane suspension (1 mg tissue/sample), 0.5 ml of [$^3$H]ligand (0.2 nM) and 20 μl of displacing agent or solvent. Non-specific binding was obtained in the presence of 100 μM (−)sulpiride.

[$^3$H]-7-OH-DPAT (specific activity 159 Ci/mmol, Amersham) binding to DA-$_3$ receptors was assayed in a final incubation volume of 1 ml, consisting of 0.5 ml of membranes suspension (10 mg tissue/sample), 0.5 ml of [$^3$H] ligand and 20 μl of displacing agent or solvent. Non-specific binding was obtained in the presence of 1 μM dopamine.

[$^3$H]Ketanserin (specific activity 63.3 Ci/mol, NEN) binding to 5-HT$_{2A}$ receptors was assayed in a final incubation volume of 1 ml consisting of 0.5 ml of membrane suspension (5 mg, tissue/sample), 0.5 ml of [$^3$H]ligand (0.7 nM) and 20 μl of displacing agent or solvent. Non-specific binding was obtained in the presence of 1 μM methysergide. Incubations (15 min at 37° C. for DA-$_2$ and 5-HT$_{2A}$ receptors; 15 min at 25° C. for DA-$_1$ receptors; 60 min at 25° C. for DA-$_3$ receptors) were stopped by rapid filtration under vacuum through GF/B (for DA-$_1$, DA-$_2$ and 5-HT$_{2A}$ receptors) or GF/C (for DA-$_3$ receptors) filters which were then washed with 12 ml of ice-cold buffer, using a Brandel M-48R. The radioactivity trapped on the filters was counted in 4 ml of Ultima Gold MV (Packard) in a LKB 1214 rack beta liquid scintillation spectrometer with a counting efficiency of 60%.

H$_1$ Affinity

Whole cortexes from male Fischer rats (300–350 g) were homogenised with a Polytron in nine volumes (w/v) of 50 mM $Na^+$—$K^+$ is phosphate buffer (pH 7.5). The homogenate was centrifuged at 16500×g for 10 min and the particulate fraction was resuspended in the original volume of buffer. In a typical experiment, aliquots of the homogenate (0.3–0.4 mg prot.) were incubated at 25° C. in 0.50 ml of the same buffer containing [$^3$H] pyrilamine (2 nM) and the displacing drags.

After 30 min of incubation, 4 ml of ice-cold buffer was added and the bound and free [$^3$H] pyrilamine were separated by filtration under vacuum through glass fiber filters (Whatman GF/B). The filters were washed three times with 4 ml of buffer, dried, placed in 15 ml of Optifluor, and counted by liquid scintillation spectrometry after a 12 h extraction period.

All assays were done in triplicate and specific binding was defined as the total amount of [$^3$H] pyrilamine bound minus that bound in the presence of $10^{-4}$M of pyrilamine. Protein concentration was determined by the Bradford method.

[$^3$H] pyrilamine, (20 ci/nmol) was obtained from New England Nuclear Corp.

Muscarinic Affinity

Male Fischer rats (300–350 g) were killed by decapitation and cortexes were rapidly removed and homogenised using a Polytron in 20 vol (w/v) of ice-cold 50 mM PBS buffer (pH 7.4). Homogenates were centrifuged at 20000×g for 15 min. The precipitated material was resuspended in assay buffer and was used for binding assay.

Triplicate incubation tubes contained [$^3$H] QNB (0.16 nM), various concentrations of drug and an aliquot of freshly resuspended tissue (~0.4 mg prot) in a final volume of 2 ml. Tubes were incubated at 37° C. for 60 min and the incubation was terminated by rapid filtration under vacuum through GF/B glass fiber filters. The filters were rinsed three times with ice-cold buffer using a Brandel filtration apparatus (Gaithersburg, Md., USA) and were placed in vials containing 15 ml of Optifluor®, cooled overnight, and counted in a liquid scintillation. Specific binding was defined as the excess over blanks containing 1 $\mu$M Atropine.

[$^3$H] QNB 42 ci/nmole was obtained from New England Nuclear Corp.

Calculations

Drugs were tested in triplicate at different concentrations, from $10^{-5}$ to $10^{-10}$ M. $IC_{50}$'s, the concentration of drug that caused 50% inhibition of [$^3$H]Ligand binding, was obtained using "Allfit" program running on an IBM personal computer.

In vivo Test

Antagonism of Apomorphine-induced Climbing in Mouse

Groups of ten mice (CD1 male) were dosed with test compounds by the subcutaneous route 30 minutes before apomorphine and placed individually into cylindrical wire mesh cages (height 14 cm, diameter 12 cm, mesh size 2 mm). Climbing behaviour was assessed at 5 min intervals for 30 min, starting 5 min after apomorphine (1.3 mg/Kg, s.c.) (Greg C. Rigdon et al. Neuropsychopharmacology Vol.15,.pp231–242 (1996)).

Antagonism of 5-MeO-DMT-induced Head Twitches in Mouse

Groups of ten mice of the CD1 strain (male) were utilised to evaluate head twitches induced by 5 methoxy-N,N-dimethyl-tryptamine (5-MeO-DMT) at a subcutaneous dosage of 10 mg/Kg.

The evaluations were begun 6 minutes from the 5-MeO-DMT and lasted 15 minutes (counting the number of head-twitches produced by the animal). The substances were administered subcutaneously 30 minutes before the 5-MeO-DMT (Greg C. Rigdon et al. Neuropsychopharmacology Vol.15,.pp231–242 (1996)).

Extrapyramidal Symptom

The test was performed on male Wistar rats (7–8 animals per group); the catalepsy evaluation was carried out by means of a metallic bar 0.6 cm in diameter positioned 10 cm from the workplace. The substances under study were administered subcutaneously 30 minutes before the first evaluation. The subsequent observations were recorded at 60, 90, 120, 180, 240, 300 minutes from administration.

The test consisted in positioning the animal with its forepaws on the bar and timing how long the animal remained hanging onto the bar employing an end-point of 60 seconds (N. A. Moore et al. Journal of Pharmacology and Experimental Therapeutics Vol. 262 pp 545–551 (1992).

Results and Discussion $D_1$, $D_2$, $D_3$ and $5HT_{2a}$ Affinity

Table 1 reports the averages and standard errors in the affinity values expressed as Ki (nM) reported by each product under study with regard to the $5HT_2$, $D_2$, $D_1$ and $D_3$ receptors.

These values were compared with the ones relative to reference compounds which are structurally similar to the compounds of the present invention (RS-Octoclothepin, R-(−)Octoclothepin; S-(+)-Octoclothepin) or belonging to the pharmacological class of the atypical antipsychotics (Olanzapine and Clozapine).

TABLE 1

| Compounds | $5HT_{2A}$ | $D_1$ | $D_2$ | $D_3$ |
|---|---|---|---|---|
| Clozapine | 11.00 ± 1.00 | 353.00 ± 35 | 250.00 ± 57 | 312.80 ± 65.07 |
| Olanzapine | 12.00 ± 1.00 | 85.00 ± 3.5 | 69.00 ± 17 | 25.80 ± 7.75 |
| RS-Octoclothepin | 0.22 ± 0.02 | 2.28 ± 0.15 | 0.36 ± 0.07 | 2.38 ± 0.37 |
| R-(−)-Octoclothepin | 0.16 ± 0.01 | 2.02 ± 0.17 | 3.64 ± 0.46 | 20.90 ± 4.35 |
| S-(+)-Octoclothepin | 0.14 ± 0.01 | 1.97 ± 0.53 | 0.40 ± 0.04 | 0.75 ± 0.12 |
| (±)-3a | 7.85 ± 2.2 | 160 ± 77 | 70 ± 17 | 57 ± 6.2 |
| ST1455 | 1.14 ± 0.12 | 27.00 ± 10 | 3.80 ± 0.5 | |
| ST1460 | 1.48 ± 0.20 | 16.40 ± 1.0 | 49.60 ± 6.0 | |
| ST1461 | 1.72 ± 0.25 | 22.00 ± 1.3 | 2.06 ± 0.2 | |
| ST1456 | 5.1 ± 0.40 | 78.00 ± 8.76 | 37.50 ± 3.01 | 12.20 ± 3.65 |
| Haloperidol | 164.10 ± 23.6 | 318.30 ± 59.2 | 4.81 ± 1.0 | 15.4 ± 3.23 |
| Methysergide | 5.3 ± 0.8 | | | |
| (−)-cis-Flupentixol | | | 37.8 ± 1.7 | |
| Sulpiride | | | 240 ± 58 | |
| Dopamine | | | | 11 ± 3.4 |

The binding evaluations relative to the compound (±)-3a, to the chloro derivative ST1455 and to the fluoro derivative ST1456, show that the substitution in position 7 with a halogen is an important condition for improving the affinities of the formula (I) compounds towards the $5HT_{2A}$ $D_2$ and $D_3$ receptors.

Relative to receptor $5-HT_{2A}$ the 7-chloro derivatives, raceme (ST 1455) and single isomers (form (+) ST1460, form (−) ST 1461) demonstrate an affinity that improves, by virtue of substitution with halogen, and proves moderately lower than the one shown by the structurally analogous reference compounds (RS-Octoclothepin, R-(−)-Octoclothepin, S-(+)-Octoclothepin) and greater to that shown by the atypical neuroleptics Clozapine and Olanzapine.

The enantiomers of the ST 1455 chloro-derivative, like those of RS-Octoclothepin, do not present significant differences of affinity towards the $5HT_{2a}$ receptor, but reveal a marked stereoselectivity of action regarding the capacity of interaction towards the dopaminergic $D_2$ receptor.

While it is observed that R-(−)-Octoclothepin shows approximately 10 times less affinity with regard to the $D_2$ receptor with respect to isoform(+), the preferred compound ST 1460, shows approximately 25 times less affinity than the (−) isomer, ST 1461.

It is therefore interesting to note that the preferred product ST 1460 presents a lower activity on the $D_2$ receptors (involved in the extrapyramidal effects), as compared to what its closest structural analogue R-(−)-Octoclothepin shows, together with an improved affinity for the $5HT_2$ and $D_1$ receptors (involved in the neuroleptic action), as compared to what the reference atypical antipsychotic Olanzapile demonstrates.

In the case of the preferred product ST 1460, it is therefore possible to obtain therapeutic effects associated with a control of extrapyramidal symptoms using lower doses with respect to those necessary for Clozapine or Olanzapine Concerning the racemic 7-fluoro derivative, ST 1456, for which has been shown an interaction capacity towards the $D_2$ receptor even below that shown by the best Octoclothepin enantiomer and towards that shown by Olanzapine, it is believed that it could possess a stereoselectivity of interaction towards the very same receptor, analogously to the racemic chloro-derivative.

Table 2 shows the inhibition constants (pKi) of the formula (I) compounds and of the reference compounds towards the $D_1$, $D_2$ $D_3$ and $5HT_2$ receptors, and the following ratios of relative affinity $D_1/D_2$ and $5HT_2/D_2$. This last value, if above 1.12, is considered a valid indication for describing the "atypical" profile of an antipsychotic (Meltzer et al. J. Pharmacol Exp. Ther 251 (1) pp 238–245 1989).

Also reported is the LogY parameter which, considering the relative affinities towards the $5HT_2$, $D_2$, and $D_1$ receptors of each product identifies and distinguishes a classic antipsychotic (Log Y>6.48) from an atypical one (Log Y<6.48) (Meltzer et al. J. Pharmacol Exp. Ther 251 (1) pp 238–245 1989).

TABLE 2

| Compound | $D_1$ pKi | $D_2$ pKi | $5HT_{2A}$ pKi | $D_1/D_2$ | $5HT_2/D_2$ | Log Y |
|---|---|---|---|---|---|---|
| Clozapine | 6.45 | 6.60 | 7.96 | 0.98 | 1.21 | 3.95 |
| Olanzapine | 7.07 | 7.16 | 7.92 | 0.99 | 1.11 | 5.43 |
| RS-Octoclothepin | 8.64 | 9.44 | 9.66 | 0.92 | 1.02 | 8.02 |
| R-(−)-Octoclothepin | 8.69 | 8.44 | 9.80 | 1.03 | 1.16 | 5.87 |
| S-(+)-Octoclothepin | 8.71 | 9.40 | 9.85 | 0.93 | 1.05 | 7.66 |
| (±)-3a | 6.8 | 7.15 | 8.1 | 0.95 | 1.13 | 4.99 |
| ST1455 | 7.57 | 8.42 | 8.94 | 0.90 | 1.06 | 6.56 |
| ST1460 | 7.79 | 7.30 | 8.83 | 1.07 | 1.21 | 4.67 |
| ST1461 | 7.66 | 8.69 | 8.76 | 0.88 | 1.01 | 7.40 |
| ST1456 | 7.11 | 7.43 | 8.29 | 0.96 | 1.12 | 5.39 |
| Haloperidol | 6.50 | 8.32 | 6.78 | 0.78 | 0.82 | 9.14 |

Observation of these results suggests that the preferred compound ST 1460 is superior to its closest structural analogue (−)-Octoclothepin (respectively 1.21 and 1.16) and different from its own racemic form ST1455 and from the isoform(−) ST 1461, for which the above-mentioned parameters describe a profile of classic antipsychotics.

Concerning a comparison with compounds having a known atypical antipsychotic activity, the relative affinity ratio $5-HT_2/D_2$ and the LogY value of the preferred compound ST 1460 describe a atypical profile comparable to that of clozapine and superior to olanzapine.

The raceme fluoro derivative ST 1456 is, unlike the racemic chloro derivative ST1455, an atypical antipsychotic comparable to the reference compound Olanzapine.

Another interesting aspect of some formula (I) compounds that emerges from an examination of the parameters represented in Table 3 is the high value of the $D_3/D_1$ receptorial affinity ratio they showed.

TABLE 3

| Compound | $D_1$ pKi | $D_3$ pKi | $D_3/D_1$ |
|---|---|---|---|
| Clozapine | 6.45 | 6.50 | 1.01 |
| Olanzapine | 7.07 | 7.59 | 1.07 |
| RS-Octoclothepin | 8.64 | 8.62 | 1.00 |
| R-(−)-Octoclothepin | 8.69 | 7.68 | 0.88 |
| S-(+)-Octoclothepin | 8.71 | 9.12 | 1.05 |
| (±)-3a | 6.8 | 7.24 | 1.07 |
| ST1456 | 7.11 | 7.91 | 1.11 |
| Haloperidol | 6.50 | 7.81 | 1.20 |

Said value is, for everyone, comparable to that determined for the reference compound Olanzapine.

Moreover, the $D_3/D_1$ value reported by formula (I) compounds clearly distinguishes them from the partially atypical neuroleptic R-(−)-Octoclothepin which shows an 0.88 activity ratio.

The relatively greater $D_3/D_1$ ratio renders formula (I) products, useful in the treatment of the negative symptoms of schizophrenia which involve the emotional and cognitive sphere, such as for is example dementia, with respect to Octoclothepin, which with its more active $D_1$ receptor is oriented towards the control of symptoms linked to muscle tone.

Affinity relative to the H1 receptors of histamine and muscarinics.

Table 4 reports the average and standard deviations of three determinations which describe the interaction capacity (Ki, nM) of each formula (I) and reference compound towards the $H_1$ receptor of Histamine and towards the muscarinic receptors.

TABLE 4

| | $H_1$ Receptor | | Muscarinic Receptors | |
|---|---|---|---|---|
| Compound | Ki (nM) | E.S. | Ki (nM) | E.S. |
| Clozapine | 14.00 | 0.00 | 54.50 | 0.00 |
| Olanzapine | 0.35 | 0.20 | 22.10 | 13.12 |
| RS-Octoclothepin | 1.00 | 0.08 | 434.10 | 31.70 |
| R-(−)-Octoclothepin | 2.32 | 0.06 | 154.60 | 12.70 |
| S-(+)-Octoclothepin | 0.62 | 0.07 | 748.60 | 87.30 |
| ST1455 | 9.46 | 1.98 | 418.20 | 47.65 |
| ST1460 | 21.33 | 12.00 | 286.40 | 13.20 |
| ST1461 | 1.40 | 0.06 | 514.50 | 154.10 |
| ST1456 | 7.33 | 1.36 | 2224.00 | 105.60 |
| Haloperidol | 384.00 | 0.00 | | |
| Pyrilamine | 12.20 | 0.09 | | |
| Atropine | | | 2.59 | 0.01 |

A study of the mentioned parameters shows that the interaction capacity of the preferred compound ST 1460 towards the $H_1$ receptor and towards the muscarinic receptors is less marked than that shown by its direct structural analog, the partially atypical neuroleptic R-(−)-Octoclothepin, and by the reference compounds of the pharmacological class of the atypical antipsychotics, Clozapine and Olanzapine.

These results render the compound ST 1460 particularly useful in the treatment of schizophrenia and distinguish it from the atypical reference compounds which, by virtue of their greater interaction capacity towards the above-mentioned receptors, associate antipsychotic efficacy with the appearance of the following side effects: dryness of the throat and the respiratory tract, constipation and weight gain. In vivo Test

TABLE 5

Dosage that determines approximately 50% climbing inhibition induced by apomorphine in the mouse

| Molecule | DOSE (MG/KG) | DOSE (µMOLES/KG) |
|---|---|---|
| Olanzapine | 0.12 | 0.38 |
| Octoclothepin RS | 0.02 | 0.043 |
| Octoclothepin R | 0.013 | 0.026 |
| Octoclothepin S | 0.041 | 0.083 |
| ST 1468 | 0.052 | 0.13 |
| ST 1469 | 0.10 | 0.24 |
| ST 1470 | 0.025 | 0.06 |

TABLE 6

Dosage that determines 50% of the Head-twitching inhibition induced by 5-MeO-DMT in the mouse

| Molecule | DOSE (MG/KG) | DOSE (µMOLES/KG) |
|---|---|---|
| Olanzapine | 0.18 | 0.58 |
| Octoclothepin RS | 0.064 | 0.14 |
| Octoclothepin R | 0.089 | 0.18 |
| Octoclothepin S | 0.079 | 0.16 |
| ST 1468 | 0.19 | 0.47 |
| ST 1469 | 0.196 | 0.49 |
| ST 1470 | 0.10 | 0.24 |

TABLE 7

Dosage that determines 100% of catalepsy in rats

| MOLECULE | DOSE (MG/KG) | DOSE (µMOLES/KG) | TIME IN MINUTES OF INSURGENCE OF CATALEPSY IN 100% OF THE ANIMALS |
|---|---|---|---|
| RS-Octoclothepin | 0.6 | 1.3 | 120 |
| R-(−)-Octoclothepin | 14.85 | 30 | 120 |
| S-(+)-Octoclothepin | 0.3 | 0.55 | 300 |
| ST 1468 | 1.22 | 3 | 180 |
| ST 1469 | >12.2 | >30 | |
| ST 1470 | 4.06 | 10 | 90 |

Table 5 shows the calculated dosage of each single compound that determines a 50% inhibition to climbing behaviour induced by apomorphine in the mouse, an indication of a dopaminergic activity.

From the results a reduction of the affinity bond which leads to an increase in dosage by the compound under study (ST 1469) can be observed both in vivo as in vitro, in that 0.1 mg/Kg (0.24 µmoles/Kg) are necessary in order to have an antagonism to the effect produced by stimulation of the dopaminergic system, of approximately 50% with respect to R-(−)-Octoclothepin whose dosage is much lower at 0.013 mg/Kg (0.026 µmoles/Kg), an indication of R-(−)-Octoclothepin's greater affinity bond.

A lesser affinity to the system classifies it as an Atypical Antipsychotic and makes it comparable to the class of drugs represented by olanzapine.

Stimulation of the serotoninergic system (table 6) by means of a non-selective agonist of serotonin receptors (5-MeO-DMT) places the compound (ST 1469) in the in vivo studies comparable to Olanzapine (0.19 mg/Kg as opposed to 0.18 mg/Kg) and with less affinity to the serotoninergic system with respect to R-(−)-Octoclothepin (0.089 mg/Kg).

The onset of the extrapyramidal syndrome (catalepsy), a negative effect of the typical neuroleptics, (see table 7) which effect should be lacking in those that are atypical, favours ST 1469 in that at a dosage corresponding to 30 µmoles/Kg R-(−)-Octoclothepin causes catalepsy in all animals after 120 minutes of treatment while the compound under study does not present catalepsy throughout the entire observation period.

From the in vivo results produced it can be concluded that ST 1469, as characterized by its demonstrated activity on the neurotransmitting systems examined and no insurgence of catalepsy, can be placed in the atypical neuroleptic class of drugs.

We claim:

1. A compound, in racemic form or as an isolated optical isomer, of formula (I):

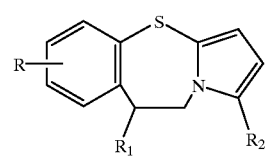

(I)

where:

R=H, Cl, Br, F, I, $C_1$–$C_4$ alkoxy, $C_1$–$C_4$ alkyltio, $C_1$–$C_4$ alkyl or $C_5$–$C_6$ cycloalkyl;

$R_1$=dialkylamine, 4-alkyl-1-piperazinyl, 4-hydroxyalkyl-1-piperazinyl, 1-imidazolyl or 4-alkyl-1-piperidinyl;

$R_2$=hydrogen, $C_1$–$C_4$ alkoxy or $C_1$–$C_4$ alkylthio; and the pharmaceutically acceptable salts thereof.

2. A compound according to claim 1, where R represents chlorine or hydrogen, $R_1$ is a 4-methyl-1-piperzinyl group; and $R_2$ is hydrogen.

3. A compound according to claim 1, where R represents fluorine, bromine or hydrogen, $R_1$ is a 4-methyl-1-piperazinyl group; and $R_2$ is hydrogen.

4. (±)-9-(4-methylpiperazin-1-yl)-9,10-dihydropyrrolo[2,1-b][1,3]benzothiaze-pine.

5. (±)-7-chloro-9-(4-methylpiperazin-1-yl)-9,10-dihydropyrrolo[2,1-b][1,3]benzothiazepine.

6. (+)-7-chloro-9-(4-methylpiperazin-1-yl)-9,10-dihydropyrrolo[2,1-b][1,3]benzothiazepine.

7. (±)-7-fluoro-9-(4-methylpiperazin-1-yl)-9,10-dihydropyrrolo[2,1-b][1,3]benzothiazepine.

8. (±)-7-fluoro-9-(4-ethylpiperazin-1-yl)-9,10-dihydropyrrolo[2,1-b][1,3]benzothiazepine.

9. (±)-7-fluoro-9-(4-hydroxyethylpiperazin-1-yl)-9,10-dihydropyrrolo[2,1-b][1,3]benzothiazepine.

10. (±)-7-Bromo-9-(4-methylpiperazin-1-yl)-9,10-dihydropyrrolo[2,1-b][1,3]benzothiazepine.

11. A process for the preparation of a compound in racemic form or as an isolated optical isomer, of formula (I):

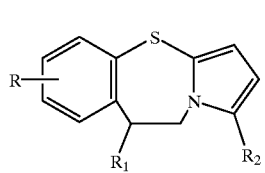

(I)

where R=H, Cl, Br, F, I, $C_1$–$C_4$ alkoxy, $C_1$–$C_4$ alkyltio, $C_1$–$C_4$ alkyl or $C_5$–$C_6$ cycloalkyl; $R_1$=dialkylamine, 4-alkyl-1-piperazinyl, 4-hydroxyalkyl-1-piperazinyl, 1-imidazolyl or 4-alkyl-1-piperidinyl; $R_2$=hydrogen, $C_1$–$C_4$ alkoxy or $C_1$–$C_4$ alkylthio; or the pharmaceutically acceptable salts thereof, said process comprising the steps of:

(a) cyclizing a derivative containing a phenyl group and a pyrrole group to form a 1,3 pyrrolobenzothiazepinone:

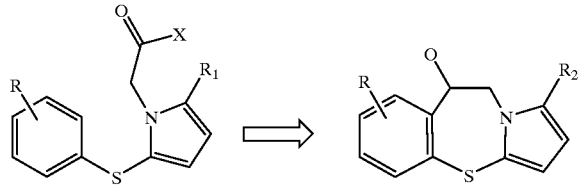

wherein X is the group MeSeO—; and (b) transforming 1,3 pyrrolobenzothiazepinone of step (a) into a compound of formula (I) by substituting the keto group on the thiazepine ring with $R_1$

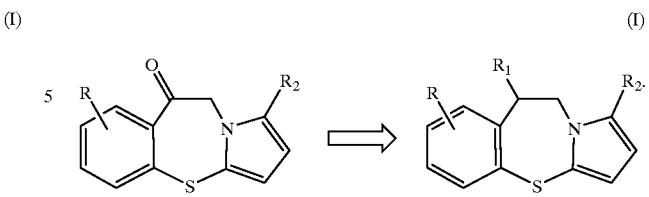

(I)

12. The process according to claim 11, where said derivative containing a phenyl group and a pyrrole group is a 1-[2-(methylsulphinyl)phenyl]-2-(pyrrol-1-yl)ethanone, and the cyclization reaction is carried out in the presence of trifluoracetic anhydride and dimethylformamide.

13. A process according to claim 11, where said derivative containing a phenyl group and a pyrrolo group is an alkyl ester of 2-(phenylthio)pyrrolo-1-selenoacetic acid and the cyclization reaction is carried out in the presence of a crystalline complex of triflate copper (I) and benzene.

14. A process for resolving the racemic compound of claim 1 into its corresponding optically active isomers comprising fractionated crystallizing the diastereoisomeric salts obtained by salification with an optically active acid.

15. A pharmaceutical composition comprising a compound of claim 1 in combination with a pharmaceutically acceptable excipient and/or vehicle.

16. The pharmaceutical composition according to claim 15, in solid or liquid form.

17. A method of treating a psychosis selected from the group consisting of schizophrenia, a paranoid state, a manic-depressive state, an affective disorder, social withdrawal, personality regression, and hallucinations, said method comprising administering to a person in need of same an effective amount of a compound of claim 1.

18. A method of treating the negative symptoms of schizophrenia involving the emotional and cognitive spheres, said method comprising administering to a person in need of same an effective amount of a compound of claim 1 provided R is hydrogen, fluorine or bromine.

19. The method according to claim 18, where the negative symptom is dementia.

* * * * *